United States Patent
Kaspar et al.

(10) Patent No.: US 9,556,257 B2
(45) Date of Patent: *Jan. 31, 2017

(54) ANTIGEN ASSOCIATED WITH RHEUMATOID ARTHRITIS

(75) Inventors: Manuela Kaspar, Brugg (CH); Kathrin Schwager, Zurich (CH); Eveline Trachsel, Hausen (CH)

(73) Assignee: PHILOGEN S.P.A., Siena (IT)

( * ) Notice: Subject to any disclaimer, the term of this patent is extended or adjusted under 35 U.S.C. 154(b) by 331 days.

This patent is subject to a terminal disclaimer.

(21) Appl. No.: 13/489,123

(22) Filed: Jun. 5, 2012

(65) Prior Publication Data

US 2012/0244114 A1 Sep. 27, 2012

Related U.S. Application Data

(63) Continuation of application No. 12/740,641, filed as application No. PCT/EP2008/009070 on Oct. 27, 2008, now Pat. No. 8,222,377.

(60) Provisional application No. 60/983,606, filed on Oct. 30, 2007.

(51) Int. Cl.
| | |
|---|---|
| A61K 38/00 | (2006.01) |
| C07K 16/18 | (2006.01) |
| A61K 47/48 | (2006.01) |
| A61K 51/10 | (2006.01) |
| A61K 39/00 | (2006.01) |

(52) U.S. Cl.
CPC ......... *C07K 16/18* (2013.01); *A61K 47/48423* (2013.01); *A61K 47/48538* (2013.01); *A61K 51/1018* (2013.01); *A61K 2039/505* (2013.01); *C07K 2317/21* (2013.01); *C07K 2317/622* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,420,012 A | 5/1995 | Partanen et al. | |
| 5,859,205 A | 1/1999 | Adair et al. | |
| 7,968,685 B2 | 6/2011 | Brack et al. | |
| 8,222,377 B2* | 7/2012 | Kaspar et al. | 530/391.7 |
| 8,263,041 B2 | 9/2012 | Rybak et al. | |
| 8,404,814 B2* | 3/2013 | Neri | C07K 14/535 424/192.1 |
| 8,481,684 B2* | 7/2013 | Rybak | A61K 51/1018 530/387.1 |
| 2002/0187100 A1 | 12/2002 | Rizzier et al. | |
| 2003/0077589 A1 | 4/2003 | Hess-Stumpp et al. | |
| 2004/0185053 A1 | 9/2004 | Govindan | |
| 2006/0024724 A1 | 2/2006 | Hussa et al. | |
| 2006/0024725 A1 | 2/2006 | Hussa et al. | |
| 2006/0024757 A1 | 2/2006 | Hussa et al. | |
| 2006/0115428 A1 | 6/2006 | Menrad et al. | |
| 2006/0188501 A1 | 8/2006 | Homma et al. | |
| 2008/0248038 A1 | 10/2008 | Corvinus et al. | |
| 2009/0068106 A1 | 3/2009 | Corti et al. | |
| 2010/0183506 A1 | 7/2010 | Neri et al. | |
| 2010/0247541 A1 | 9/2010 | Rybak et al. | |
| 2010/0260707 A1 | 10/2010 | Kaspar et al. | |
| 2011/0250131 A1 | 10/2011 | Schwager | |
| 2012/0244114 A1 | 9/2012 | Kaspar et al. | |
| 2012/0251439 A1 | 10/2012 | Schwager | |

FOREIGN PATENT DOCUMENTS

| | | |
|---|---|---|
| EP | 0344134 | 5/1989 |
| EP | 0580859 | 2/1994 |
| EP | 0603735 | 6/1994 |
| RU | 2280254 | 2/2005 |
| WO | WO 01/83816 | 11/2001 |
| WO | WO 0220563 | 3/2002 |
| WO | WO 02/057290 | 7/2002 |
| WO | WO 04/000216 | 12/2003 |
| WO | WO 2004/067038 | 8/2004 |
| WO | WO 2004/094612 | 11/2004 |
| WO | WO 2005/009366 | 2/2005 |
| WO | WO-2005066348 | 7/2005 |
| WO | WO 2005/086612 | 9/2005 |
| WO | WO 2006/026020 | 3/2006 |
| WO | WO 2006/050834 | 5/2006 |
| WO | WO 2006/119897 | 11/2006 |
| WO | WO 2007/128563 | 11/2007 |
| WO | WO 2008/120101 | 10/2008 |
| WO | WO 2009/013619 | 1/2009 |
| WO | WO 2009/056268 | 5/2009 |
| WO | WO-2010078945 | 7/2010 |
| WO | WO-2010078950 | 7/2010 |

OTHER PUBLICATIONS

David et al. Molecular Immunology, 2007. 44:1342-1351.*
Clark et al. The Journal of Immunology, 2006. 177:333-340.*
Bose and Sinha. Immunology, 2005. 116:172-183.*
Gerlag et al. Suppression of murine collagen-induced arthritis by targeted apoptosis of synovial neovasculature. Arthritis Res 2001, 3:357-361.*
Galeazzi et al. A Phase IB Clinical Trial with Dekavil (F8-IL10), an Immunoregulatory 'Armed Antibody' for the Treatment of Rheumatoid Arthritis, Used in Combination with Methotrexate. IMAJ 2014; 16: 666.*
Chevalier et al., Presence of ED-A containing fibronectin in human articular cartilage from patients with osteoarthritis and rheumatoid arthritis. J Rheumatol. Jun. 1996;23(6):1022-30. Abstract.*
Carsons, S. Extra domain-positive fibronectins in arthritis: wolf in sheep's clothing. Rheumatology 2001; 40:721-723.*
Decision on Grant Patent for Invention, Russian Patent Application No. 2010121874, 7 pages (Nov. 1, 2012).
Aguayo et al., "Angiogenesis in acute and chronic leukemias and myelodysplastic syndromes," *Blood*, vol. 96, No. 6, pp. 2240-2245, 2000.

(Continued)

*Primary Examiner* — Maher Haddad
(74) *Attorney, Agent, or Firm* — Ropes & Gray LLP

(57) ABSTRACT

The invention relates to a binding member that binds the Extra Domain-A (ED-A) isoform of fibronectin for the detection and treatment of rheumatoid arthritis.

31 Claims, 9 Drawing Sheets

(56) References Cited

OTHER PUBLICATIONS

Ballard et al., "Vascular tenascin-C regulates cardiac endothelial phenotype and neovascularization," *The FASEB Journal*, vol. 20, No. 6, pp. 717-719, 2006.
Balza et al., "Transforming growth factor β regulates the levels of different fibronectin isoforms in normal human cultured fibroblasts," *FEBS Letters*, vol. 228, No. 1, pp. 42-44, 1988.
Berndt et al., "Differential expression of tenascin-C splicing domains in urothelial carcinomas of the urinary bladder," *J. Cancer Res. Clin. Oncol.*, vol. 132, pp. 537-546, 2006.
Berndt et al., "Evidence of ED-B$^+$ fibronectin synthesis in human tissues by non-radioactive RNA in situ hybridization. Investigations on carcinoma (oral squamous cell and breast carcinoma), chronic inflammation (rheumatoid synovitis) and fibromatosis (Morbus Dupuytren)," *Histochem. Cell Biol.*, vol. 109, pp. 249-255, 1998.
Birchler et al., "Infrared photodetection for the in vivo localisation of phage-derived antibodies directed against angiogenic markers," *Journal of Immunological Methods*, vol. 231, pp. 239-248, 1999.
Birchler et al., "Selective targeting and photocoagulation of ocular angiogenesis mediated by a phage-derived human antibody fragment," *Nature Biotechnology*, vol. 17, pp. 984-988, 1999.
Borsi et al., "Monoclonal Antibodies in the Analysis of Fibronectin Isoforms Generated by Alternative Splicing of mRNA Precursors in Normal and Transformed Human Cells," *Journal of Cell Biology*, vol. 104, pp. 595-600, 1987.
Borsi et al., "Preparation of Phage Antibodies to the ED-A Domain of Human Fibronectin," *Experimental Cell Research*, vol. 240, pp. 244-251, 1998.
Borsi et al., "Selective Targeting of Tumoral Vasculature: Comparison of Different Formats of an Antibody (L19) to the ED-B Domain of Fibronectin," *Int. J. Cancer*, vol. 102, pp. 75-85, 2002.
Borsi et al., "The Alternative Splicing Pattern of the Tenascin-C Pre-mRNA Is Controlled by the Extracellular pH," *Journal of Biological Chemistry*, vol. 270, No. 11, pp. 6243-6245, 1995.
Borsi et al., "Transforming growth factor-β regulates the splicing pattern of fibronectin messenger RNA precursor," *FEBS Letters*, vol. 261, No. 1, pp. 175-178, 1990.
Brack et al., "Tumor-Targeting Properties of Novel Antibodies Specific to the Large Isoform of Tenascin-C," *Clinical Cancer Research*, vol. 12, No. 10, pp. 3200-3208, 2006.
Brown et al., "Tolerance of single, but not multiple, amino acid replacements in antibody VH CDR2: a means of minimizing B cell wastage from somatic hypermutation?" *J. Immuno.*, pp. 3285-3291, 1996.
Carnemolla et al., "A Tumor-associated Fibronectin Isoform Generated by Alternative Splicing of Messenger RNA Precursors," *Journal of Cell Biology*, vol. 108, pp. 1139-1148, 1989.
Carnemolla et al., "Identification of a Glioblastoma-Associated Tenascin-C Isoform by a High Affinity Recombinant Antibody," *American Journal of Pathology*, vol. 154, No. 5, pp. 1345-1352, 1999.
Carnemolla et al., "Phage Antibodies with Pan-Species Recognition of the Oncofoetal Angiogenesis Marker Fibronectin ED-B Domain," *Int. J. Cancer*, vol. 68, pp. 397-405, 1996.
Castellani et al., "The Fibronectin Isoform Containing the ED-B Oncofetal Domain: A Marker of Angiogenesis," *Int. J. Cancer*, vol. 59, pp. 612-618, 1994.
Chevalier et al., "Presence of ED-A Containing Fibronectin in Human Articular Cartilage from Patients with Osteoarthritis and Rheumatoid Arthritis," *The Journal of Rheumatology*, vol. 23, No. 6, pp. 1022-1030, 1996.
Chilosi et al., "Constitutive Expression of Tenascin in T-Dependent Zones of Human Lymphoid Tissues," *American Journal of Pathology*, vol. 143, No. 5, pp. 1348-1355, 1993.
Claudepierre et al., "Increased Ed-B fibronectin plasma levels in spondyloarthropathies: comparison with rheumatoid arthritis patients and a healthy population," *Rheumatology*, vol. 38, No. 11, pp. 1099-1103, 1999.

Davies et al., "Affinity improvement of single antibody VH domains: residues in all three hypervariable regions affect antigen binding," *Immunotechnology*, vol. 2, pp. 169-179, 1996.
Demartis et al., "Selective targeting of tumour neovasculature by a radiohalogenated human antibody fragment specific for the ED-B domain of fibronectin," *Eur. J. Nucl. Med.*, vol. 28, pp. 534-539, 2001.
Dickerson et al., "Enhancement of the Antianglogenic Activity of Interleukin-12 by Peptide Targeted Delivery of the Cytokine to $a_v\beta_3$ Integrin," *Mol. Cancer Res.*, vol. 2, line 12, pp. 663-673, 2004.
El-Sorady et al., "Bone Marrow Angiogenesis in Patients with Hematological Malignancies: Role of VEGF," *Journal of the Egyptian Nat. Cancer Inst.*, vol. 12, No. 2, pp. 131-136, 2000.
Estey, "Modulation of angiogenesis in patients with myelodysplastic syndrome," *Best Practice & Research Clinical Haematology*, vol. 17, No. 4, pp. 623-639, 2004.
Fabbrini et al., "Selective occlusion of tumor blood vessels by targeted delivery of an antibody-photosensitizer conjugate," *Int. J. Cancer*, vol. 118, pp. 1805-1813, 2006.
Giovannoni et al., "Isolation of anti-angiogenesis antibodies from a large combinatorial repertoire by colony filter screening," *Nucleic Acids Research*, vol. 29, No. 5, p. e27 (1-6), 2001.
Hanahan et al., "The hallmarks of cancer," *Cell*, vol. 100, No. 1, pp. 57-70, 2000.
Holt et al., "Domain antibodies: proteins for therapy," *Trends in Biotechnology*, vol. 21, No. 11, pp. 484-490, 2003.
Kaspar et al., "Fibronectin as target for tumor therapy," *Int. J. Cancer*, vol. 118, pp. 1331-1339, 2006.
Kauma et al., "Production of Fibronectin by Peritoneal Macrophages and Concentration of Fibronectin in Peritoneal Fluid from Patients With or Without Endometriosis," *Obstetrics & Gynecology*, vol. 72, No. 1, pp. 13-18, 1988.
Kriegsmann et al., "Expression of fibronectin splice variants and oncofetal glycosylated fibronectin in the synovial membranes of patients with rheumatoid arthritis and osteoarthritis," *Rheumatol. Int.*, vol. 24, pp. 25-33, 2004.
Liao et al., "The EIIIA Segment of Fibronectin Is a Ligand for Integrins$\alpha_9\beta_1$ and $\alpha_4\beta_1$ Providing a Novel Mechanism for Regulating Cell Adhesion by Alternative Splicing," *Journal of Biological Chemistry*, vol. 277, No. 17, pp. 14467-14474, 2002.
Linnala et al., "Isoforms of cellular fibronectin and tenascin in amniotic fluid," *FEBS Letters*, vol. 337, pp. 167-170, 1994.
Marlind et al., "Antibody-Mediated Delivery of Interleukin-2 to the Stroma of Breast Cancer Strongly Enhances the Potency of Chemotherapy," *Clin. Cancer Res.*, vol. 14, No. 20, pp. 6515-6524, 2008.
Matter et al., "Molecular Imaging of Atherosclerotic Plaques Using a Human Antibody Against the Extra-Domain B of Fibronectin," *Circulation Research*, vol. 95, pp. 1225-1233, 2004.
Neri et al., "Tumour Vascular Targeting," *Nature Rev. Cancer*, vol. 5, pp. 436-446, 2005.
Nilsson et al., "Targeted Delivery of Tissue Factor to the ED-B Domain of Fibronectin, a Marker of Angiogenesis, Mediates the Infarction of Solid Tumors in Mice," *Cancer Research*, vol. 61, pp. 711-716, 2001.
Okamura et al., "The Extra Domain A of Fibronectin Activates Toll-like Receptor 4," *Journal of Biological Chemistry*, vol. 276, No. 13, pp. 10229-10233, 2001.
Oyama et al., "Deregulation of Alternative Splicing of Fibronectin Pre-mRNA in Malignant Human Liver Tumors," *Journal of Biological Chemistry*, vol. 264, No. 18, pp. 10331-10334, 1989.
Oyama et al., "Oncodevelopmental Regulation of the Alternative Splicing of Fibronectin Pre-Messenger RNA in Human Lung Tissues," *Cancer Research*, vol. 50, No. 4, pp. 1075-1078, 1990.
Padro et al., "Increased angiogenesis in the bone marrow of patients with acute myeloid leukemia," *Blood*, vol. 95, No. 8, pp. 2637-2644, 2000.
Paganelli et al., "Pre-targeted immunodetection in glioma patients: tumour localization and single-photon emission tomography imaging of [$^{99m}$Tc]PnAO-biotin," *Eur. J. Nucl. Med.*, vol. 21, pp. 314-321, 1994.
Paul, William E., Fundamental Immunology, 3$^{rd}$ Edition, 1993, pp. 292-295.

(56) References Cited

OTHER PUBLICATIONS

Peters et al., "Preferential Recognition of a Fragment Species of Osteoarthritic Synovial Fluid Fibronectin by Antibodies to the Alternatively Spliced EIIIA Segment," *Arthritis and Rheumatism*, vol. 44, No. 11, pp. 2572-2585, 2001.
Riva et al., "Local Treatment of Malignant Gliomas by Direct Infusion of Specific Monoclonal Antibodies Labeled with $^{131}$I: Comparison of the Results Obtained in Recurrent and Newly Diagnosed Tumors," *Cancer Research*, vol. 55, pp. 5952s-5956s, 1995.
Riva et al., "Treatment of Intracranial Human Glioblastoma by Direct Intratumoral Administration of $_{131}$I-Labelled Anti-Tenascin Monoclonal Antibody BC-2," *Int. J. Cancer*, vol. 51, pp. 7-13, 1992.
Rudkoff et al., "Single amino acid substitution altering antigen-binding specificity," *PNAS U.S.A.*, vol. 79, No. 6, pp. 1979-1983, 1982.
Rybak et al., "Ligand-Based Vascular Targeting of Disease," *ChemMedChem*, vol. 2, pp. 22-40, 2007.
Rybak et al., "The Extra-domain A of Fibronectin Is a Vascular Marker of Solid Tumors and Metastases," *Cancer Research*, vol. 67, No. 22, pp. 10948-10957, 2007.
Scarpino et al., "Expression of EDA/EDB Isoborms of Fibronectin in Papillary Carcinoma of the Thyroid," *Journal of Pathology*, vol. 188, pp. 163-167, 1999.
Schliemann et al., "Complete eradication of human B-cell lymphoma xenografts using rituximab in combination with the immunocytokine L19-IL2," *Blood*, vol. 113, pp. 2275-2283, 2009.
Schliemann et al., "Three clinical-stage tumor targeting antibodies reveal differential expression of oncofetal fibronectin and tenascin-C isoforms in human lymphoma," *Leukemia Research*, vol. 33, pp. 1718-1722, 2009.
Schrama et al., "Antibody targeted drugs as cancer therapeutics," *Nature Rev. Drug Disc.*, vol. 5, pp. 147-159, 2006.
Schwager et al., "Preclinical characterization of DEKAVIL (F8-IL10), a novel clinical-stage immunocytokine which inhibits the progression of collagen-induced arthritis," *Arthritis and Research Therapy*, vol. 11, R142, 2009.
Shiozawa et al., "Alternatively spliced EDA-containing fibronectin in synovial fluid as a predictor of rheumatoid joint destruction," *Rheumatology*, vol. 40, pp. 739-742, 2001.
Smolej and Kasparova, "Choice of endothelial marker is crucial for assessment of bone marrow microvessel density in chronic lymphocytic leukemia," *APMIS*, vol. 116, No. 12, pp. 1058-1062, 2008.
Soini et al., "Tenascin immunoreactivity in normal and pathological bone marrow," *Journal of Clinical Pathology*, vol. 46, No. 3, pp. 218-221, 1993.
Tarli et al., "A High-Affinity Human Antibody That Targets Tumoral Blood Vessels," *Blood*, vol. 94, No. 1, pp. 192-198, 1999.
Taylor et al., "VEGF and imaging of vessels in rheumatoid arthritis," *Arthritis Research*, vol. 4, Supp. 3, pp. s99-s107, 2002.
Thorpe, "Vascular Targeting Agents as Cancer Therapeutics," *Clinical Cancer Research*, vol. 10, pp. 415-427, 2004.
Trachsel et al., "A Human mAb Specific to Oncofetal Fibronectin Selectively Targets Chronic Skin Inflammation in vivo," *Journal of Investigative Dermatology*, vol. 127, pp. 881-886, 2007.
Trachsel et al., "Antibodies for angiogenesis inhibition, vascular targeting and endothelial cell transcytosis," *Advanced Drug Delivery Reviews*, vol. 58, pp. 735-754, 2007.
Trachsel et al., "Antibody-mediated delivery of IL-10 inhibits the progression of established collagen-induced arthritis," *Arthritis Research and Therapy*, vol. 9, No. 1, R9, 2007.
Vajdos et al., "Comprehensive functional maps of the antigen-binding site of an anti-ErbB2 obtained with shotgun scanning mutagenesis," *J. Mol. Biol.*, vol. 320, No. 2, pp. 415-428, 2002.
Vartio et al., "Differential expression of the ED sequence-containing form of cellular fibronectin in embryonic and adult human tissues," *J. Cell Sci.*, vol. 88, pp. 419-430, 1987.

Villa et al., "A high-affinity human monoclonal antibody specific to the alternatively spliced EDA domain of fibronectin efficiently targets tumor neo-vasculature in vivo," *Int. J. Cancer*, vol. 122, pp. 2405-2413, 2008.
Viti et al., "Increased Binding Affinity and Valence of Recombinant Antibody Fragments Lead to Improved Targeting of Tumoral Angiogenesis," *Cancer Research*, vol. 59, pp. 347-352, 1999.
Walsh et al., "Focally Regulated Endothelial Proliferation and Cell Death in Human Synovium," *American Journal of Pathology*, vol. 152, No. 3, pp. 691-702, 1998.
Wang et al., "Identification of a Mutated Fibronectin As a Tumor Antigen Recognized by CD4$^+$ T Cells: Its Role in Extracellular Matrix Formation and Tumor Metastasis," *The Journal of Experimental Medicine*, vol. 195, No. 11, pp. 1397-1406, 2002.
Doll et al., "Murine analogues of etanercept and of F8-IL 10 inhibit the progression of collagen-induced arthritis in the mouse," Arthritis Res. Ther. 15(5):R138 (2013).
Fiechter et al., "Comparative in vivo analysis of the atherosclerotic plaque targeting properties of eight human monoclonal antibodies," *Atherosclerosis* 214(2):325-330 (2011).
Franz et al., "Selective imaging of chronic cardiac rejection using a human antibody specific to the alternatively spliced EDA domain of fibronectin," *J. Heart Lung Transplant.* 32(6):641-650 (2013).
Galeazzi et al., "A phase Ib clinical trial in rheumatoid arthritis of Dekavil (F8-IL10), a novel antiflammatory immunocytokine," EULAR Annual European Congress of Rheumatology, 2014, Poster SAT0232, Paris, France, Jun. 11-14, 2014.
Pasche and Neri, "Immunocytokines: a novel class of potent armed antibodies," Drug Discov Today, 17 (11-12):583-590 (2012).
Schwager et al., "The antibody-mediated targeted delivery of interleukin-10 inhibits endometriosis in a syngeneic mouse model," Hum. Reprod. 26(9) 2344-2352 (2011).
Tamura et al., "Structural correlates of an anticarcinoma antibody: identification of specificity-determining residues (SDRs) and development of a minimally immunogenic antibody variant by retention of SDRs only," J. Immunol., 164:1432-1441 (2000).
Van De Loo and Van Den Berg, "Immunocytokines: the long awaited therapeutic magic bullet in rheumatoid arthritis?" Arthritis Res. Ther. 11(6):132 (2009).
Schwager et al., "A comparative immunofluorescence analysis of three clinical-stage antibodies in head and neck cancer, " Head & Neck Oncology, 3:25 (2011).
Adams et al., "High affinity restricts the localization and tumor penetration of single-chain fv antibody molecules," Cancer Res., 61:4750-4755 (2001).
Allie, A search service for abbreviation / long form, p. 1, Jun. 27, 2012.
Astrof et al., "Direct test of potential roles of EIIIA and EIIIB alternatively spliced segments of fibronectin in physiological and tumor angiogenesis," Mol Cell Biol., 24:8662-8670 (2004).
Auerbach et al., "Angiogenesis assays: problems and pitfalls," Cancer Metastasis Rev., 19:167-172 (2000).
Beguin et al., "Soluble CD23 and other receptors (CD4, CD8, CD25, CD71) in serum of patients with chronic lymphocytic leukemia," Leukemia., 7:2019-2025 (1993).
Berndorff et al., "Imaging of tumor angiogenesis using 99mTc-labeled human recombinant anti-ED-B fibronectin antibody fragments," J Nucl Med., 47:1707-1716 (2006).
Berndorff et al., "Radioimmunotherapy of solid tumors by targeting extra domain B fibronectin: identification of the best-suited radioimmunoconjugate," Clin Cancer Res., 11:7053s-7063s (2005).
Bootz et al., "Alternatively Spliced EDA Domain of Fibronectin Is a Target for Pharmacodelivery Applications in Inflammatory Bowel Disease," 21:1908-1917 (2015).
Borsi et al., "Expression of different tenascin isoforms in normal, hyperplastic and neoplastic human breast tissues," *Int J. Cancer.*, 52:688-692 (1992).
Brenmoehl et al., "Evidence for a differential expression of fibronectin splice forms ED-A and ED-B in Crohn's disease (CD) mucosa," Int. J. Colorectal Dis., 22:611-623 (2007).
Brenmoehl et al., "Inflammation modulates fibronectin isoform expression in colonic lamina propria fibroblasts (CLPF)," Int. J. Colorectal Dis., 23:947-955 (2008).

(56) References Cited

OTHER PUBLICATIONS

Burrows et al., "Up-regulation of endoglin on vascular endothelial cells in human solid tumors: implications for diagnosis and therapy," Clin Cancer Res., 1:1623-1634 (1995).
Carnemolla et al., "Enhancement of the antitumor properties of interleukin-2 by its targeted delivery to the tumor blood vessel extracellular matrix," Blood, 99:1659-1665 (2002).
Castellani et al., "Transformed human cells release different fibronectin variants than do normal cells," J Cell Biol., 103:1671-1677 (1986).
Castronovo et al., "A chemical proteomics approach for the identification of accessible antigens expressed in human kidney cancer," Mol Cell Proteomics, 5:2083-2091 (2006).
Clamp et al., "The clinical potential of antiangiogenic fragments of extracellular matrix proteins," Br J Cancer, 93:967-972 (2005).
Cseh et al., "Cell surface fibronectin on peripheral blood lymphocytes in normal individuals and in patients with acute and chronic lymphocytic leukemia and non Hodgkin's lymphoma," Allergol Immunopathol (Madr)., 13:35-40 (1985).
D'Ovidio et al., "Intratumoral microvessel density and expression of ED-A/ED-B sequences of fibronectin in breast carcinoma," Eur J. Cancer, 34:1081-1085 (1998).
Dr. Andrew C.R. Martin's Group, Antibody General Information V1.0 [online], Jul. 16, 1997, [retrieved on Oct. 26, 2015], Retrieved from the Internet, URL, http://www.biochem.ucl.ac.uk/_martin/abs/GeneralInfo.html.
Franz et al., "Targeted delivery of interleukin-10 to chronic cardiac allograft rejection using a human antibody specific to the extra domain A of fibronectin," Int J Cardiol., 195:311-322 (2015).
Gafner et al., "An engineered antibody-interleukin-12 fusion protein with enhanced tumor vascular targeting properties," Int J. Cancer, 119:2205-2212 (2006).
Halin et al., "Enhancement of the antitumor activity of interleukin-12 by targeted delivery to neovasculature," Nat Biotechnol., 20:264-269 (2002).
Halin et al., "Tumor-targeting properties of antibody-vascular endothelial growth factor fusion proteins," Int J Cancer, 102:109-116 (2002).
Hussein et al., "Opposite expression pattern of Src kinase Lyn in acute and chronic haematological malignancies," Ann Hematol., 88:1059-1067 (2009).
Karp et al., "Targeting vascular endothelial growth factor for relapsed and refractory adult acute myelogenous leukemias: therapy with sequential 1-beta-d-arabinofuranosylcytosine, mitoxantrone, and bevacizumab," Clin Cancer Res., 10:3577-3585 (2004).
Kato et al., "A new type of antimetastatic peptide derived from fibronectin," Clin Cancer Res., 8:2455-2462 (2002).
Luster et al., "Plasma protein beta-2-glycoprotein 1 mediates interaction between the anti-tumor monoclonal antibody 3G4 and anionic phospholipids on endothelial cells," J Biol Chem., 281:29863-29871 (2006).
Mariani et al., "Tumor targeting potential of the monoclonal antibody BC-1 against oncofetal fibronectin in nude mice bearing human tumor implants," Cancer, 80:2378-2384 (1997).
Marlow et al., "Why interleukin-10 supplementation does not work in Crohn's disease patients," World J Gastroenterol., 19:3931-3941 (2013).
Menrad et al., "ED-B fibronectin as a target for antibody-based cancer treatments," Expert Opin Ther Targets, 9:491-500 (2005).
Neri et al., "Interfering with pH regulation in tumours as a therapeutic strategy," Nat Rev Drug Discov., 10:767-777 (2011).
Niesner et al., "Quantitation of the tumor-targeting properties of antibody fragments conjugated to cell-permeating HIV-1 TAT peptides," Bioconjug Chem., 13:729-736 (2002).
Olive et al., "Endometriosis," N Engl J Med., 328:1759-1769 (1993).
Oyama et al., "Coordinate oncodevelopmental modulation of alternative splicing of fibronectin pre-messenger RNA at ED-A, ED-B, and CS1 regions in human liver tumors," Cancer Res., 53:2005-2011 (1993).
Padlan, "Anatomy of the antibody molecule," Mol Immunol., 31:169-217 (1994).
Padro et al., "Overexpression of vascular endothelial growth factor (VEGF) and its cellular receptor KDR (VEGFR-2) in the bone marrow of patients with acute myeloid leukemia," Leukemia., 16:1302-1310 (2002).
Pasche et al., "Cloning and characterization of novel tumor-targeting immunocytokines based on murine IL7," J Biotechnol., 154:84-92 (2011).
Pasche et al., "The antibody-based delivery of interleukin-12 to the tumor neovasculature eradicates murine models of cancer in combination with paclitaxel," Clin Cancer Res., 18:4092-4103 (2012).
Payne, "Progress in immunoconjugate cancer therapeutics," Cance Cell, 3:207-212 (2003).
Rodig et al., "Heterogeneous CD52 expression among hematologic neoplasms: implications for the use of alemtuzumab (CAMPATH-1H)," Clin Cancer Res., 2:7174-7179 (2006).
Santimaria et al., "Immunoscintigraphic detection of the ED-B domain of fibronectin, a marker of angiogenesis, in patients with cancer," Clin Cancer Res., 9:571-579 (2003).
Silacci et al., "Human monoclonal antibodies to domain C of tenascin-C selectively target solid tumors in vivo," Protein Eng Des Sel., 19:471-478 (2006).
Smith et al., "Computerized analysis of tumor cell interactions with extracellular matrix proteins, peptides, and endothelial cells under laminar flow," Biotechnol Bioeng., 50:598-607 (1996).
Sommavilla et al., "Expression, engineering and characterization of the tumor-targeting heterodimeric immunocytokine F8-IL12," Protein Eng Des Sel., 23:653-661 (2010).
Spaeth et al., "Radioimmunotherapy targeting the extra domain B of fibronectin in C6 rat gliomas: a preliminary study about the therapeutic efficacy of iodine-131-labeled SIP(L19)," Nucl Med Biol., 33:661-666 (2006).
Tagashira et al., "Interleukin-10 attenuates TNF-alpha-induced interleukin-6 production in endometriotic stromal cells," Fertil Steril., 91:2185-2192 (2009).
Tijink et al., "Radioimmunotherapy of head and neck cancer xenografts using 131I-labeled antibody L19-SIP for selective targeting of tumor vasculature," J Nucl Med., 47:1127-1135 (2006).
Varma et al., "Endometriosis and the neoplastic process," Reproduction, 127:293-304 (2004).
Wallace et al., "Media hype and drug discovery," Drug Discovery Today 3:433-434 (1998).
Zardi et al., "Transformed human cells produce a new fibronectin isoform by preferential alternative splicing of a previously unobserved exon," EMBO J., 6:2337-2342 (1987).

\* cited by examiner

FIG 3

A   1 NIDRPKGLAFTDVDVDSIKIAWESPQGQVSRYRVTYSSPEDGTHELFPAPDGEEDTAELQ
      ************************************************************
B   1 NIDRPKGLAFTDVDVDSIKIAWESPQGQVSRYRVTYSSPEDGIRELFPAPDGEDDTAELQ

A  61 GLRPGSEYTVSVVALHDDMESQPLIGTQST  (SEQ ID NO: 118)
      *****************************
B  61 GLRPGSEYTVSVVALHDDMESQPLIGIQST  (SEQ ID NO: 119)

FIG 4A

GAGGTGCAGCTGGTGGAGTCTGGGGGAGGCTTGGTACAGCCTG
GGGGGTCCCTGAGACTCTCCTGTGCAGCCTCTGGATTCACCTT
TAGCCCGCGGAGGATGAGCTGGGTCCGCCAGGCTCCAGGGAAG
GGGCTGGAGTGGGTCTCAGCTATTAGTGGTAGTGGTGGTAGCA
CATACTACGCAGACTCCGTGAAGGGCCGGTTCACCATCTCCAG
AGACAATTCCAAGAACACGCTGTATCTGCAAATGAACAGCCTG
AGAGCCGAGGACACGGCCGTATATTACTGTGCGAAAAGTACTC
ATTTGTATCTTTTTGACTACTGGGGCCAGGGAACCCTGGTCAC
CGTCTCGAGT  (SEQ ID NO: 12)

FIG 4B

GGCGGTGGAGGTTCTGGCGGCGGTGGCAGTGGCGGTGGAGGTT
CCGGGGGTGGAGGATCT  (SEQ ID NO: 14)

FIG 4C

GAAATTGTGTTGACGCAGTCTCCAGGCACCCTGTCTTTGTCTC
CAGGGGAAAAAGCCACCCTCTCCTGCAGGGCCAGTCAGAGTGT
TAGCTCTGCGTGGTTAGCCTGGTACCAGCAGAAACCTGGCCAG
GCTCCCAGGCTCCTCATCTATGGTGCATCCAGCAGGGCCACTG
GCATCCAGACAGGTTCAGTGGCAGTGGGTCTGGGACAGACTT
CACTCTCACCATCAGCAGACTGGAGCCTGAAGATTTTGCAGTG
TATTACTGTCAGCAGATGCGTGGTCGGCCGCCGACGTTCGGCC
AAGGGACCAAGGTGGAAATCAAAGCGGCCGCAGAACAAAAACT
CATCTCAGAAGAGGATCTGAATGGGGCCGCATAGACTGTGAAA (SEQ ID NO: 13)

FIG 5A

EVQLVESGGGLVQPGGSLRLSCAASGFTFS<u>PRRM</u>SWVRQ
APGKGLEWVSAI*SGSGGS*TYYADSVKGRFTISRDNSKNT
LYLQMNSLRAEDTAVYYCAK<u>STHLYL</u>FDYWGQGTLVTVS
S    (SEQ ID NO: 1)

FIG 5B

GGGGSGGGGSGGGGSGGGGS    (SEQ ID NO: 11)

FIG 5C

EIVLTQSPGTLSLSPGEKATLSCRASQSVS<u>SAWLA</u>WYQQ
KPGQAPRLLIY*GASSRAT*GIPDRFSGSGSGTDFTLTISR
LEPEDFAVYYCQQ<u>MRGRPP</u>TFGQGTKVEIKAAAEQKLIS
EEDLNGAA    (SEQ ID NO: 2)

FIG 6

AAGCTTGTCGACCATGGGCTGGAGCCTGATCCTCCTGTTCCTCGTCGCTGTGG
CTACAGGTAAGGGGCTCACAGTAGCAGGCTTGAGGTCTGGACATATATATGGG
TGACAATGACATCCACTTTGCCTTTCTCTCCACAGGTGTGCACTCGGAGGTGCA
GCTGTTGGAGTCTGGGGGAGGCTTGGTACAGCCTGGGGGGTCCCTGAGACTC
TCCTGTGCAGCCTCTGGATTCACCTTTAGCCTGTTTACGATGAGCTGGGTCCG
CCAGGCTCCAGGGAAGGGGCTGGAGTGGGTCTCAGCTATTAGTGGTAGTGGT
GGTAGCACATACTACGCAGACTCCGTGAAGGGCCGGTTCACCATCTCCAGAG
ACAATTCCAAGAACACGCTGTATCTGCAAATGAACAGCCTGAGAGCCGAGGA
CACGGCCGTATATTACTGTGCGAAAAGTACTCATTTGTATCTTTTTGACTACTG
GGGCCAGGGAACCCTGGTCACCGTCTCGAGTggtggaggcggttcaggcggaggtggc
tctggcggtggcggaGAAATTGTGTTGACGCAGTCTCCAGGCACCCTGTCTTTGTCT
CCAGGGGAAAGAGCCACCCTCTCCTGCAGGGCCAGTCAGAGTGTTAGCATGC
CGTTTTTAGCCTGGTACCAGCAGAAACCTGGCCAGGCTCCCAGGCTCCTCAT
CTATGGTGCATCCAGCAGGGCCACTGGCATCCCAGACAGGTTCAGTGGCAGT
GGGTCTGGGACAGACTTCACTCTCACCATCAGCAGACTGGAGCCTGAAGATT
TTGCAGTGTATTACTGTCAGCAGATGCGTGGTCGGCCGCCGACGTTCGGCCA
AGGGACCAAGGTGGAAATCAAAGAATTC*TCTTCCTCATCGGGTAGTAGCTCTT*
*CCGGCTCATCGTCCAGCGGCAGCCCAGGCCAGGGCACCCAGTCTGAGAACAG*
*CTGCACCCACTTCCCAGGCAACCTGCCTAACATGCTTCGAGATCTCCGAGATG*
*CCTTCAGCAGAGTGAAGACTTTCTTTCAAATGAAGGATCAGCTGGACAACTTGT*
*TGTTAAAGGAGTCCTTGCTGGAGGACTTTAAGGGTTACCTGGGTTGCCAAGCCT*
*TGTCTGAGATGATCCAGTTTTACCTGGAGGAGGTGATGCCCCAAGCTGAGAAC*
*CAAGACCCAGACATCAAGGCGCATGTGAACTCCCTGGGGGAGAACCTGAAGAC*
*CCTCAGGCTGAGGCTACGGCGCTGTCATCGATTTCTTCCCTGTGAAAACAAGA*
*GCAAGGCCGTGGAGCAGGTGAAGAATGCCTTTAATAAGCTCCAAGAGAAAGGC*
*ATCTACAAGCCATGAGTGAGTTTGACATCTTCATCAACTACATAGAAGCCTACA*
*TGACAATGAAGATACGAAAC*taatgaGCGGCCGC (SEQ. ID NO: 148)

FIG 7

EVQLLESGGG LVQPGGSLRL SCAASGFTFS LFTMSWVRQA PGKGLEWVSA

ISGSGGSTYY ADSVKGRFTI SRDNSKNTLY LQMNSLRAED TAVYYCAKST

HLYLFDYWGQ GTLVTVssgg ggsggggsgg ggEIVLTQSP GTLSLSPGER

ATLSCRASQS VSMPFLAWYQ QKPGQAPRLL IYGASSRATG IPDRFSGSGS

GTDFTLTISR LEPEDFAVYY CQQMRGRPPT FGQGTKVEIK Efssssgsss sgssssgSPG QGTQSENSCT HFPGNLPNML RDLRDAFSRV KTFFQMKDQL

DNLLLKESLL EDFKGYLGCQ ALSEMIQFYL EEVMPQAENQ DPDIKAHVNS

LGENLKTLRL RLRRCHRFLP CENKSKAVEQ VKNAFNKLQE KGIYKAMSEF

DFINYIEAY MTMKIRN  (SEQ. ID NO: 149)

ANTIGEN ASSOCIATED WITH RHEUMATOID ARTHRITIS

CROSS-REFERENCE TO RELATED APPLICATIONS

This is a continuation of U.S. patent application Ser. No. 12/740,641, filed Apr. 29, 2010, now U.S. Pat. No. 8,222,377, which is the §371 U.S. National Stage of International Application No. PCT/EP2008/009070, filed Oct. 27, 2008, which was published in English under PCT Article 21(2), which in turn claims priority to U.S. Provisional Patent Application No. 60/983,606, filed Oct. 30, 2007, all of which are incorporated by reference herein in their entirety.

JOINT RESEARCH AGREEMENT

The claimed invention was made pursuant to a written joint research agreement between Philogen S.p.A. and Philochem AG, that was in effect on or before the date the invention was made.

FIELD OF THE INVENTION

The present invention relates to the detection and treatment of rheumatoid arthritis (RA). The invention involves use of a binding member that binds the ED-A isoform of fibronectin, especially a binding member that binds domain ED-A of fibronectin.

BACKGROUND OF THE INVENTION

Rheumatoid arthritis (RA) is a chronic inflammatory and destructive joint disease that affects 0.5-1% of the population in the industrialized world and commonly leads to significant disability and a consequent reduction in quality of life.

Angiogenesis in the synovial membrane of patients with RA is considered to be an important early step in pathogenesis and in the perpetuation of disease (Taylor, 2002). As in neoplastic disease, angiogenesis feeds the expanding synovium (Walsh et al., 1998). Blood vessel growth probably contributes to the proliferation of the inflammatory synovial pannus as well as to the ingress of inflammatory leukocytes into the synovial tissue. Synovium of patients with RA contained increased amounts of fibroblast growth factor-2 (FGF-2) and of vascular endothelial growth factor (VEGF) (Koch, 2003). Serum VEGF concentrations correlate with disease activity and fall, when synovitis is successfully suppressed by therapy (Taylor, 2002).

Fibronectin (FN) is a glycoprotein and is widely expressed in a variety of normal tissues and body fluids. It is a component of the extracellular matrix (ECM), and plays a role in many biological processes, including cellular adhesion, cellular migration, haemostasis, thrombosis, wound healing, tissue differentiation and oncogenic transformation.

Different FN isoforms are generated by alternative splicing of three regions (ED-A, ED-B, IIICS) of the primary transcript FN pre-mRNA, a process that is modulated by cytokines and extracellular pH (Balza 1988; Carnemolla 1989; Borsi 1990; Borsi 1995). Fibronectin contains two type-III globular extra-domains which may undergo alternative splicing: ED-A and ED-B (ffrench-Constant 1995, Hynes 1990, Kaspar et al. 2006). The ED-As of mouse fibronectin and human fibronectin are 96.7% identical (only 3 amino acids differ between the two 90 amino acid sequences, see FIG. 2).

Expression of the ED-A of fibronectin has been reported in tumour cells and in solid tumours at the mRNA level in breast cancer (Jacobs et al. 2002, Matsumoto et al. 1999) and liver cancer (Oyama et al. 1989, Tavian et al. 1994) and at the level of isolated protein in fibrosarcoma, rhabdomyosarcoma and melanoma (Borsi et al. 1987).

At the immunohistochemical level, the presence of ED-A has been detected in the extracellular matrix (ECM) of odontogenic tumours (Heikinheimo et al. 1991) and hepatocellular carcinoma (Koukoulis et al. 1995). In contrast, ED-A has been detected in the stroma of malignant breast neoplasms (Koukoulis et al. 1993), and in the blood vessels and basement membranes of well-differentiated renal cell carcinoma (Lohi et al. 1995). However, in less-differentiated renal cell carcinoma (Lohi et al. 1995) and papillary carcinoma of the thyroid (Scarpino et al. 1999) ED-A has been detected in the blood vessels, basement membranes and tumour stroma. The presence of ED-A in the vasculature of gliomas has also been reported (Borsi et al. 1998). Thus, the pattern of ED-A expression reported for different types of tumours is highly variable.

Antibody-based targeted delivery of bioactive agents to sites of angiogenesis is an attractive therapeutic strategy for cancer treatment, but is largely unexplored for chronic inflammatory diseases. We have previously demonstrated that the ED-B domain of fibronectin, a marker of angiogenesis, is expressed in psoriatic lesions in patients and in a mouse model of psoriasis as well as in arthritic paws in the collagen-induced mouse model of rheumatoid arthritis. Using both radioactive and fluorescent techniques, the human monoclonal antibody L19, specific to EDB, was found to selectively localize at sites of inflammation in vivo, following intravenous administration. These results suggest a therapeutic potential for the L19-based selective delivery of bioactive compounds to sites of inflammation (Trachsel, 2007; PCT/EP2007/004044).

It has been shown before by in-situ-hybridisation that other than ED-B also the ED-A domain of fibronectin can be present in human arthritic specimens (Berndt et al., 1998; Kriegsmann et al., 2004).

SUMMARY OF THE INVENTION

We show herein that anti-EDA antibody, such as the F8 antibody disclosed herein, is able to give a stronger staining pattern on human arthritic specimens compared with the anti-EDB-antibody L19 and the anti-tenascin-C antibodies F16 and G11.

Furthermore, using both radioactive and fluorescent techniques, the human monoclonal antibody F8, specific to ED-A, was found to selectively localize at sites of inflammation in vivo, following intravenous administration.

Accordingly, ED-A of fibronectin is indicated as a vascular marker of rheumatoid arthritis.

Binding molecules such as antibody molecules that bind the A-FN and/or the ED-A of fibronectin represent novel agents which may be used for the preparation of a medicament for the treatment of rheumatoid arthritis (RA).

This invention provides the use of a binding member, e.g. an antibody molecule, that binds the Extra Domain-A (ED-A) isoform of fibronectin (A-FN), for the preparation of a medicament for the treatment of rheumatoid arthritis. The invention also provides the use of a binding member, e.g. an antibody molecule, that binds the ED-A of fibronectin for the preparation of a medicament for the treatment of rheumatoid arthritis.

The invention further provides the use of a binding member, e.g. an antibody molecule, that binds the ED-A isoform of fibronectin for delivery, to sites of rheumatoid arthritis, of a molecule conjugated to the binding member. The invention also provides the use of a binding member, e.g. an antibody molecule, that binds the ED-A of fibronectin for delivery, to sites of rheumatoid arthritis, of a molecule conjugated to the binding member. The binding member may be used for the manufacture of a medicament for delivery of such a molecule.

The invention provides the use of a binding member, e.g. an antibody molecule, that binds the ED-A isoform of fibronectin for the manufacture of a diagnostic product for use in diagnosing rheumatoid arthritis. The invention also provides the use of a binding member, e.g. an antibody molecule, that binds the ED-A of fibronectin for the manufacture of a diagnostic product for use in diagnosing rheumatoid arthritis.

The invention further provides a method of detecting or diagnosing rheumatoid arthritis in a human or animal comprising:
(a) administering to the human or animal a binding member, e.g. an antibody molecule, which binds the ED-A of fibronectin, and
(b) determining the presence or absence of the binding member in sites of rheumatoid arthritis of the human or animal body; wherein localisation of the binding member to sites of rheumatoid arthritis indicates the presence of rheumatoid arthritis.

The present invention provides a method of treating rheumatoid arthritis in an individual comprising administering to the individual a therapeutically effective amount of a medicament comprising a binding member, e.g. an antibody molecule, which binds the ED-A isoform of fibronectin. The present invention also provides a method of treating rheumatoid arthritis in an individual comprising administering to the individual a therapeutically effective amount of a medicament comprising a binding member, e.g. an antibody molecule, which binds the ED-A of fibronectin.

The present invention provides a composition comprising a binding member, e.g. an antibody molecule, which binds the ED-A isoform of fibronectin, for use in a method of treating rheumatoid arthritis in an individual comprising administering to the individual a therapeutically effective amount of a medicament comprising a binding member, e.g. an antibody molecule, which binds the ED-A isoform of fibronectin. The present invention also provides a composition comprising a binding member, e.g. an antibody molecule, which binds the ED-A of fibronectin, for use in a method of treating rheumatoid arthritis in an individual comprising administering to the individual a therapeutically effective amount of a medicament comprising a binding member, e.g. an antibody molecule, which binds the ED-A of fibronectin.

The invention provides a method of delivering a molecule to the neovasculature of sites of rheumatoid arthritis in a human or animal comprising administering to the human or animal a binding member, e.g. an antibody molecule, which binds the ED-A isoform of fibronectin, wherein the binding member is conjugated to the molecule. The invention also provides a method of delivering a molecule to the neovasculature of sites of rheumatoid arthritis in a human or animal comprising administering to the human or animal a binding member, e.g. an antibody molecule which binds the ED-A of fibronectin, wherein the binding member is conjugated to the molecule.

A binding member for use in the invention may be an antibody which binds the ED-A isoform of fibronectin and/or the ED-A of fibronectin, comprising one or more complementarity determining regions (CDRs) of antibody H1, B2, C5, D5, E5, C8, F8, F1, B7, E8 or G9, or variants thereof. Preferably, a binding member for use in the invention is an antibody which binds the ED-A isoform of fibronectin and/or the ED-A of fibronectin, comprising one or more complementarity determining regions (CDRs) of antibody B2, C5, D5, C8, F8, B7 or G9, or variants thereof. Most preferably, a binding member for use in the invention is an antibody which binds the ED-A isoform of fibronectin and/or the ED-A of fibronectin, comprising one or more complementarity determining regions (CDRs) of antibody F8 or variants thereof.

A binding member for use in the invention may comprise a set of H and/or L CDRs of antibody H1, B2, C5, D5, E5, C8, F8, F1, B7, E8 or G9, or a set of H and/or L CDRs of antibody H1, B2, C5, D5, E5, C8, F8, F1, B7, E8 or G9 with ten or fewer, e.g. one, two, three, four, or five, amino acid substitutions within the disclosed set of H and/or L CDRs. Preferably, a binding member for use in the invention comprises a set of H and/or L CDRs of antibody B2, C5, D5, C8, F8, B7 or G9 with ten or fewer, e.g. one, two, three, four, or five, amino acid substitutions within the disclosed set of H and/or L CDRs. Preferably, a binding member for use in the invention comprises a set of H and/or L CDRs of antibody F8 with ten or fewer, e.g. one, two, three, four, or five, amino acid substitutions within the disclosed set of H and/or L CDRs.

Substitutions may potentially be made at any residue within the set of CDRs, and may be within CDR1, CDR2 and/or CDR3.

For example, a binding member for use in the invention may comprise one or more CDRs as described herein, e.g. a CDR3, and optionally also a CDR1 and CDR2 to form a set of CDRs.

A binding member for use in the invention may also comprise an antibody molecule, e.g. a human antibody molecule. The binding member normally comprises an antibody VH and/or VL domain. VH domains of binding members are also provided for use in the invention. Within each of the VH and VL domains are complementarity determining regions, ("CDRs"), and framework regions, ("FRs"). A VH domain comprises a set of HCDRs, and a VL domain comprises a set of LCDRs. An antibody molecule may comprise an antibody VH domain comprising a VH CDR1, CDR2 and CDR3 and a framework. It may alternatively or also comprise an antibody VL domain comprising a VL CDR1, CDR2 and CDR3 and a framework. The VH and VL domains and CDRs of antibodies H1, B2, C5, D5, E5, C8, F8, F1, B7, E8 and G9 are described herein. All VH and VL sequences, CDR sequences, sets of CDRs and sets of HCDRs and sets of LCDRs disclosed herein represent embodiments of a binding member for use in the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs.

A binding member for use in the invention may comprise an antibody VH domain comprising complementarity determining regions HCDR1, HCDR2 and HCDR3 and a framework, wherein HCDR1 is SEQ ID NO: 3, 23, 33, 43, 53, 63, 73, 83, 93, 103 or 113, and wherein optionally HCDR2 is SEQ ID NO: 4 and/or HCDR3 is SEQ ID NO: 5. Preferably, the HCDR1 is SEQ ID NO: 23, 33, 43, 53, 73, 83 or 103. Most preferably, the HCDR1 is SEQ ID NO: 83.

Typically, a VH domain is paired with a VL domain to provide an antibody antigen-binding site, although as discussed further below a VH or VL domain alone may be used to bind antigen. Thus, a binding member for use in the invention may further comprise an antibody VL domain comprising complementarity determining regions LCDR1, LCDR2 and LCDR3 and a framework, wherein LCDR1 is SEQ ID NO: 6, 26, 36, 46, 56, 66, 76, 86, 96, 106 or 116 and wherein optionally LCDR2 is SEQ ID NO: 7 and/or LCDR3 is SEQ ID NO: 8. Preferably, the LCDR1 is SEQ ID NO: 26, 36, 46, 56, 76, 86 or 106. Most preferably, the LCDR1 is SEQ ID NO: 86.

A binding member for use in the invention may be an isolated antibody molecule for the ED-A of fibronectin, comprising a VH domain and a VL domain, wherein the VH domain comprises a framework and a set of complementarity determining regions HCDR1, HCDR2 and HCDR3 and wherein the VL domain comprises complementarity determining regions LCDR1, LCDR2 and LCDR3 and a framework, and wherein HCDR1 has amino acid sequence SEQ ID NO: 3, 23, 33, 43, 53, 63, 73, 83, 93, 103 or 113,
HCDR2 has amino acid sequence SEQ ID NO: 4,
HCDR3 has amino acid sequence SEQ ID NO: 5,
LCDR1 has amino acid sequence SEQ ID NO: 6, 26, 36, 46, 56, 66, 76, 86, 96, 106 or 116;
LCDR2 has amino acid sequence SEQ ID NO: 7; and
LCDR3 has amino acid sequence SEQ ID NO: 8.

One or more CDRs or a set of CDRs of an antibody may be grafted into a framework (e.g. human framework) to provide an antibody molecule for use in the invention. Framework regions may comprise human germline gene segment sequences. Thus, the framework may be germlined, whereby one or more residues within the framework are changed to match the residues at the equivalent position in the most similar human germline framework. A binding member for use in the invention may be an isolated antibody molecule having a VH domain comprising a set of HCDRs in a human germline framework, e.g. DP47. Normally the binding member also has a VL domain comprising a set of LCDRs, e.g. in a human germline framework. The human germline framework of the VL domain may be DPK22.

A VH domain for use in the invention may have amino acid sequence SEQ ID NO: 1, 21, 31, 41, 51, 61, 71, 81, 91, 101 or 111. Preferably, a VH domain for use in the invention has amino acid sequence SEQ ID NO: 21, 31, 41, 51, 71, 81 or 101. Most preferably, a VH domain for use in the invention has amino acid sequence SEQ ID NO: 81. A VL domain for use in the invention may have the amino acid SEQ ID NO: 2, 22, 32, 42, 52, 62, 72, 82, 92, 102 or 112. Preferably, a VL domain for use in the invention has amino acid SEQ ID NO: 22, 32, 42, 52, 72, 82 or 102. Most preferably, a VL domain for use in the invention has amino acid SEQ ID NO: 82.

A binding member for use in the invention may be or comprise a single chain Fv (scFv), comprising a VH domain and a VL domain joined via a peptide linker. The skilled person may select an appropriate length and sequence of linker, e.g. at least 5 or 10 amino acids in length, up to about 15, 20 or 25 amino acids in length. The linker may have the amino acid sequence GSSGG (SEQ ID NO: 28). The scFv may consist of or comprise amino acid sequence SEQ ID NO: 9.

A single chain Fv (scFv) may be comprised within a mini-immunoglobulin or small immunoprotein (SIP), e.g. as described in (Li et al., 1997). A sip may comprise an scFv molecule fused to the CH4 domain of the human IgE secretory isoform IgE-S2 ($\epsilon_{s2}$-CH4; Batista et al., 1996) forming an homo-dimeric mini-immunoglobulin antibody molecule.

Alternatively, a binding member for use in the invention may comprise an antigen-binding site within a non-antibody molecule, normally provided by one or more CDRs e.g. a set of CDRs in a non-antibody protein scaffold. Binding members, including non-antibody and antibody molecules, are described in more detail elsewhere herein.

A binding member for use in the invention may be conjugated to a molecule that has biocidal, cytotoxic immunosuppressive or anti-inflammatory activity. Interleukin-10 is an advantageous molecule for conjugation with a binding member in accordance with the present invention, and useful in treatment of rheumatoid arthritis. Furthermore, a binding member for use in the invention may be conjugated to a radioisotope, a detectable lable or a photosensitizer.

These and other aspects of the invention are described in further detail below.

BRIEF DESCRIPTION OF THE FIGURES

FIG. 3 shows an alignment between A: the human ED-A (top sequence) and B: the mouse ED-A (bottom sequence). The asterisks indicate the amino acid positions where the amino acids of the human ED-A and the mouse ED-A are identical.

FIG. 4A shows the nucleotide sequence of the anti-ED-A antibody H1 heavy chain (VH) (SEQ ID NO: 12). The nucleotide sequence of the heavy chain CDR1 of anti-ED-A antibody H1 is underlined. The nucleotide sequence of the heavy chain CDR2 of the anti-ED-A antibody H1 is shown in italics and underlined. The nucleotide sequence of the heavy chain CDR3 of anti-ED-A antibody H1 is shown in bold and underlined.

FIG. 4B shows the nucleotide sequence of the anti-ED-A antibody H1 linker sequence (SEQ ID NO: 14).

FIG. 4C shows the nucleotide sequence of the anti-ED-A antibody H1 light chain (VL) (SEQ ID NO: 13). The nucleotide sequence of the light chain CDR1 of anti-ED-A antibody H1 is underlined. The nucleotide sequence of the light chain CDR2 of the anti-ED-A antibody H1 is shown in italics and underlined. The nucleotide sequence of the light chain CDR3 of anti-ED-A antibody H1 is shown in bold and underlined.

FIG. 5A shows the amino acid sequence of the anti-ED-A antibody H1 heavy chain (VH) (SEQ ID NO: 1). The amino acid sequence of the heavy chain CDR1 (SEQ ID NO: 3) of anti-ED-A antibody H1 is underlined. The amino acid sequence of the heavy chain CDR2 (SEQ ID NO: 4) of the anti-ED-A antibody H1 is shown in italics and underlined. The amino acid sequence of the heavy chain CDR3 (SEQ ID NO: 5) of anti-ED-A antibody H1 is shown in bold and underlined.

FIG. 5B shows the amino acid sequence of the anti-ED-A antibody H1 linker sequence (SEQ ID NO: 11).

FIG. 5C shows the amino acid sequence of the anti-ED-A antibody H1 light chain (VL) (SEQ ID NO: 2). The amino acid sequence of the light chain CDR1 (SEQ ID NO: 6) of anti-ED-A antibody H1 is underlined. The amino acid sequence of the light chain CDR2 (SEQ ID NO: 7) of the anti-ED-A antibody H1 is shown in italics and underlined. The amino acid sequence of the light chain CDR3 (SEQ ID NO: 8) of anti-ED-A antibody H1 is shown in bold and underlined.

FIG. 6 shows the sequence of a nucleic acid construct including a coding sequence for F8-IL10. The structure is HINDIII Secretion sequence F8 (14aa linker) linker (SSSSG)$_3$—IL10-Stop-NotI, as follows: a HINDIII restriction site is underlined, sequence encoding the secretion signal is in italics, the F8 VH-encoding sequence is in bold following the secretion signal sequence, sequence encoding the 14 amino acid linker is in lower case, F8 VL-encoding sequence is in bold following the 14 amino acid linker sequence, a linker (SSSSG)$_3$ (amino acids 243-257 of SEQ ID NO: 149) sequence follows the F8 encoding sequence underlined and in italics, the IL-10 encoding sequence is double-underlined; stop is then in lower case, followed by a NOTI restriction site that is underlined.

FIG. 7 shows the amino acid sequence of an antibody scFv (F8) IL-10 conjugate, including linkers, of structure: VH-linker-VL-linker-IL-10. The VH and VL domains are in bold, the scFv linker is in lower case, the linker between scFv and IL10 is in lower case and italics, the IL-10 sequence is underlined.

FIG. 8a shows a schematic representation of a pcDNA3.1 vector containing the elements of the F8-IL10 fusion proteins. The human IL10 moiety was fused to the C-terminus of the scFv antibody fragment by the 15 amino acid linker (SSSSG)$_3$ (amino acids 243-257 of SEQ ID NO: 149). The secretion sequence at the N-terminus is required for secretion of recombinant proteins.

FIG. 8b shows the results of SDS-PAGE analysis of purified fusion proteins: Lane 1, molecular weight marker; lanes 2 & 3, F8-IL10 under non-reducing and reducing conditions. The monomeric fusion protein is expected to have a molecular weight of 46 kDa.

FIG. 8c shows a size exclusion chromatography profile of purified F8-IL10 (Superdex 200). The peak eluting at 13 ml retention volume corresponds to the non-covalent homodimeric form of F8-IL10, the smaller peak eluting at 14 ml retention volume corresponds to the monomeric fraction.

FIG. 8d shows the results of an activity assay of F8-IL10. The activity of F8-IL10 was compared with that of recombinant human IL10 on MC/9 cells.

DETAILED DESCRIPTION OF THE INVENTION

Figure 1:
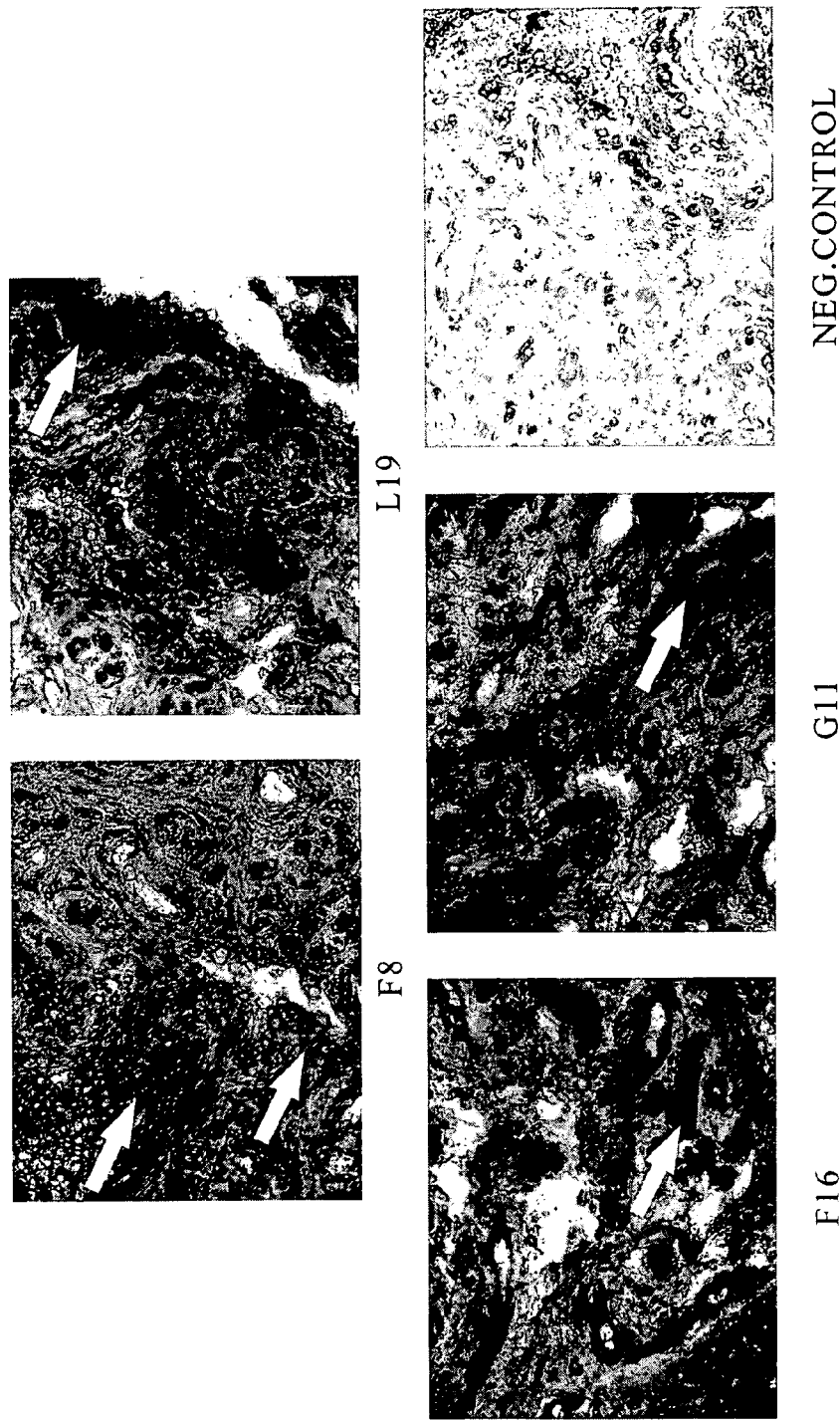
FIG. 1 shows the results of immunohistochemistry on human arthritic specimens using antibodies directed to markers of angiogenesis. Darker staining indicates strong expression of the antigen, visualized by white arrows. F8 is an antibody molecule that binds ED-A, disclosed herein, L19 is an antibody molecule that binds ED-B (e.g. Pini et al. 1998), F16 and G11 are antibody molecules that bind Tenascin-C domains A1 and C, respectively (WO2006/050834).

Terminology
Fibronectin

Fibronectin is an antigen subject to alternative splicing, and a number of alternative isoforms of fibronectin are known, as described elsewhere herein. Extra Domain-A (EDA or ED-A) is also known as ED, extra type III repeat A (EIIIA) or EDI. The sequence of human ED-A has been published by Kornblihtt et al. (1984), Nucleic Acids Res. 12, 5853-5868 and Paolella et al. (1988), Nucleic Acids Res. 16, 3545-3557. The sequence of human ED-A is also available on the SwissProt database as amino acids 1631-1720 (Fibronectin type-III 12; extra domain 2) of the amino acid sequence deposited under accession number P02751. The sequence of mouse ED-A is available on the SwissProt database as amino acids 1721-1810 (Fibronectin type-III 13; extra domain 2) of the amino acid sequence deposited under accession number P11276.

The ED-A isoform of fibronectin (A-FN) contains the Extra Domain-A (ED-A). The sequence of the human A-FN can be deduced from the corresponding human fibronectin precursor sequence which is available on the SwissProt database under accession number P02751. The sequence of the mouse A-FN can be deduced from the corresponding mouse fibronectin precursor sequence which is available on the SwissProt database under accession number P11276. The A-FN may be the human ED-A isoform of fibronectin. The ED-A may be the Extra Domain-A of human fibronectin.

ED-A is a 90 amino acid sequence which is inserted into fibronectin (FN) by alternative splicing and is located between domain 11 and 12 of FN (Borsi et al., 1987, J. Cell Biol., 104, 595-600). ED-A is mainly absent in the plasma form of FN but is abundant during embryogenesis, tissue remodelling, fibrosis, cardiac transplantation and solid tumour growth.

Alternative Splicing

Alternative splicing refers to the occurrence of different patterns of splicing of a primary RNA transcript of DNA to produce different mRNAs. After excision of introns, selection may determine which exons are spliced together to form the mRNA. Alternative splicing leads to production of different isoforms containing different exons and/or different numbers of exons. For example one isoform may comprise an additional amino acid sequence corresponding to one or more exons, which may comprise one or more domains.

Binding Member

This describes one member of a pair of molecules that bind one another. The members of a binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, biotin-avidin, hormone-hormone receptor, receptor-ligand, enzyme-substrate. The present invention is concerned with antigen-antibody type reactions.

A binding member normally comprises a molecule having an antigen-binding site. For example, a binding member may be an antibody molecule or a non-antibody protein that comprises an antigen-binding site.

An antigen binding site may be provided by means of arrangement of complementarity determining regions (CDRs) on non-antibody protein scaffolds such as fibronectin or cytochrome B etc. (Haan & Maggos, 2004; Koide 1998; Nygren 1997), or by randomising or mutating amino acid residues of a loop within a protein scaffold to confer binding specificity for a desired target. Scaffolds for engineering novel binding sites in proteins have been reviewed in detail by Nygren et al. (1997). Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties such as an ability to enter cells, penetrate deep into tissues or reach targets within other structures, or to bind within protein cavities of the target antigen. Use of antigen binding sites in non-antibody protein scaffolds is reviewed in Wess, 2004. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, tetranectin, fibronectin (e.g. 10th fibronectin type III domain) and lipocalins. Other approaches include synthetic "Microbodies" (Selecore GmbH), which are based on cyclotides—small proteins having intra-molecular disulphide bonds.

In addition to antibody sequences and/or an antigen-binding site, a binding member for use in the present invention may comprise other amino acids, e.g. forming a peptide or polypeptide, such as a folded domain, or to impart to the molecule another functional characteristic in addition to ability to bind antigen. Binding members for use in the invention may carry a detectable label, or may be conjugated to a toxin or a targeting moiety or enzyme (e.g. via a peptidyl bond or linker). For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by non-antibody scaffolds, the structure for carrying a CDR or a set of CDRs will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat 1987, and updates thereof, now available on the Internet (at immuno.bme.nwu.edu or find "Kabat" using any search engine).

By CDR region or CDR, it is intended to indicate the hypervariable regions of the heavy and light chains of the immunoglobulin as defined by Kabat et al. (1987), (Kabat 1991a, and later editions). An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It can be as short as 2 amino acids although the longest size known is 26. Functionally, HCDR3 plays a role in part in the determination of the specificity of the antibody (Segal 1974; Amit 1986; Chothia 1987; Chothia 1989; Caton 1990; Sharon 1990a; Sharon 1990b; Kabat et al., 1991b).

Antibody Molecule

This describes an immunoglobulin whether natural or partly or wholly synthetically produced. The term also relates to any polypeptide or protein comprising an antibody antigen-binding site. It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described later. Antibody fragments that comprise an antibody antigen-binding site include, but are not limited to, antibody molecules such as Fab, Fab', Fab'-SH, scFv, Fv, dAb, Fd; and diabodies.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any binding member or substance having an antibody antigen-binding site with the required specificity and/or binding to antigen. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described in EP-A-0120694 and EP-A-0125023, and a large body of subsequent literature.

Further techniques available in the art of antibody engineering have made it possible to isolate human and humanised antibodies. For example, human hybridomas can be made as described by Kontermann & Dubel (2001). Phage display, another established technique for generating binding members has been described in detail in many publications such as WO92/01047 (discussed further below) and U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160, 6,521,404 and Kontermann & Dubel (2001). Transgenic mice in which the mouse antibody genes are inactivated and functionally replaced with human antibody genes while leaving intact other components of the mouse immune system, can be used for isolating human antibodies (Mendez 1997).

Synthetic antibody molecules may be created by expression from genes generated by means of oligonucleotides synthesized and assembled within suitable expression vectors, for example as described by Knappik et al. (2000) or Krebs et al. (2001).

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward 1989; McCafferty 1990; Holt 2003), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird 1988; Huston 1988); (viii) bispecific single chain Fv dimers (PCT/US92/09965) and (ix) "diabodies", multivalent or multispecific fragments constructed by gene fusion (WO94/13804; Holliger 1993a). Fv, scFv or diabody molecules may be stabilized by the incorporation of disulphide bridges linking the VH and VL domains (Reiter 1996). Minibodies comprising a scFv joined to a CH3 domain may also be made (Hu 1996). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

Antibody fragments for use in the invention can be obtained starting from any of the antibody molecules described herein, e.g. antibody molecules comprising VH and/or VL domains or CDRs of any of antibodies described herein, by methods such as digestion by enzymes, such as pepsin or papain and/or by cleavage of the disulfide bridges by chemical reduction. In another manner, antibody fragments of the present invention may be obtained by techniques of genetic recombination likewise well known to the person skilled in the art or else by peptide synthesis by means of, for example, automatic peptide synthesizers such as those supplied by the company Applied Biosystems, etc., or by nucleic acid synthesis and expression.

Functional antibody fragments according to the present invention include any functional fragment whose half-life is increased by a chemical modification, especially by PEGylation, or by incorporation in a liposome.

A dAb (domain antibody) is a small monomeric antigen-binding fragment of an antibody, namely the variable region of an antibody heavy or light chain (Holt 2003). VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. A binding member of the present invention may be a dAb comprising a VH or VL domain substantially as set out herein, or a VH or VL domain comprising a set of CDRs substantially as set out herein.

As used herein, the phrase "substantially as set out" refers to the characteristic(s) of the relevant CDRs of the VH or VL domain of binding members described herein will be either identical or highly similar to the specified regions of which the sequence is set out herein. As described herein, the phrase "highly similar" with respect to specified region(s) of one or more variable domains, it is contemplated that from 1 to about 5, e.g. from 1 to 4, including 1 to 3, or 1 or 2, or 3 or 4, amino acid substitutions may be made in the CDR and/or VH or VL domain.

Bispecific or bifunctional antibodies form a second generation of monoclonal antibodies in which two different variable regions are combined in the same molecule (Holliger 1999). Their use has been demonstrated both in the diagnostic field and in the therapy field from their capacity to recruit new effector functions or to target several molecules on the surface of tumor cells. Where bispecific antibodies are to be used, these may be conventional bispecific antibodies, which can be manufactured in a variety of ways (Holliger 1993b), e.g. prepared chemically or from hybrid hybridomas, or may be any of the bispecific antibody fragments mentioned above. These antibodies can be obtained by chemical methods (Glennie 1987; Repp 1995) or somatic methods (Staerz 1986; Suresh 1986) but likewise by genetic engineering techniques which allow the heterodimerization to be forced and thus facilitate the process of purification of the antibody sought (Merchand 1998). Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against a target antigen, then a library can be made where the other arm is varied and an antibody of appropriate specificity selected. Bispecific whole antibodies may be made by alternative engineering methods as described in Ridgeway 1996.

Various methods are available in the art for obtaining antibodies against a target antigen. The antibodies may be monoclonal antibodies, especially of human, murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" (Harlow and Lane 1988) or to the technique of preparation from hybridomas described by Kohler and Milstein, 1975.

Monoclonal antibodies can be obtained, for example, from an animal cell immunized against A-FN, or one of its fragments containing the epitope recognized by said monoclonal antibodies, e.g. a fragment comprising or consisting of ED-A, or a peptide fragment of ED-A. The A-FN, or one of its fragments, can especially be produced according to the usual working methods, by genetic recombination starting with a nucleic acid sequence contained in the cDNA sequence coding for A-FN or fragment thereof, by peptide synthesis starting from a sequence of amino acids comprised in the peptide sequence of the A-FN and/or fragment thereof.

Monoclonal antibodies can, for example, be purified on an affinity column on which A-FN or one of its fragments containing the epitope recognized by said monoclonal antibodies, e.g. a fragment comprising or consisting of ED-A or a peptide fragment of ED-A, has previously been immobilized. Monoclonal antibodies can be purified by chromatography on protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. The whole of these techniques may be used simultaneously or successively.

Antigen-Binding Site

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site may comprise an antibody light chain variable region (VL) and an antibody heavy chain variable region (VH).

Isolated

This refers to the state in which binding members for use in the invention or nucleic acid encoding such binding members, will generally be in accordance with the present invention. Thus, binding members, VH and/or VL domains of the present invention may be provided isolated and/or purified, e.g. from their natural environment, in substantially pure or homogeneous form, or, in the case of nucleic acid, free or substantially free of nucleic acid or genes of origin other than the sequence encoding a polypeptide with the required function. Isolated members and isolated nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

Heterogeneous preparations comprising antibody molecules may also be used in the invention. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

One or more binding members for an antigen, e.g. the A-FN or the ED-A of fibronectin, may be obtained by bringing into contact a library of binding members according to the invention and the antigen or a fragment thereof, e.g. a fragment comprising or consisting of ED-A or a peptide fragment of ED-A and selecting one or more binding members of the library able to bind the antigen.

An antibody library may be screened using Iterative Colony Filter Screening (ICFS). In ICFS, bacteria containing the DNA encoding several binding specificities are grown in a liquid medium and, once the stage of exponential growth has been reached, some billions of them are distributed onto a growth support consisting of a suitably pre-treated membrane filter which is incubated until completely confluent bacteriae colonies appear. A second trap substrate consists of another membrane filter, pre-humidified and covered with the desired antigen.

The trap membrane filter is then placed onto a plate containing a suitable culture medium and covered with the growth filter with the surface covered with bacterial colonies pointing upwards. The sandwich thus obtained is incubated at room temperature for about 16 h. It is thus possible to obtain the expression of the genes encoding antibody fragments scFv having a spreading action, so that those fragments binding specifically with the antigen which is present on the trap membrane are trapped. The trap membrane is then treated to point out bound antibody fragments scFv with colorimetric techniques commonly used to this purpose.

The position of the coloured spots on the trap filter allows to go back to the corresponding bacterial colonies which are present on the growth membrane and produced the antibody fragments trapped. Such colonies are gathered and grown and the bacteria—a few millions of them are distributed onto a new culture membrane repeating the procedures described above. Analogous cycles are then carried out until the positive signals on the trap membrane correspond to single positive colonies, each of which represents a potential source of monoclonal antibody fragments directed against the antigen used in the selection. ICFS is described in e.g. WO0246455, which is incorporated herein by reference.

A library may also be displayed on particles or molecular complexes, e.g. replicable genetic packages such bacteriophage (e.g. T7) particles, or other in vitro display systems, each particle or molecular complex containing nucleic acid encoding the antibody VH variable domain displayed on it, and optionally also a displayed VL domain if present. Phage display is described in WO92/01047 and e.g. U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160 and 6,521,404, each of which is herein incorporated by reference in its entirety.

Following selection of binding members able to bind the antigen and displayed on bacteriophage or other library particles or molecular complexes, nucleic acid may be taken from a bacteriophage or other particle or molecular complex displaying a said selected binding member. Such nucleic acid may be used in subsequent production of a binding member or an antibody VH or VL variable domain by expression from nucleic acid with the sequence of nucleic acid taken from a bacteriophage or other particle or molecular complex displaying a said selected binding member.

An antibody VH variable domain with the amino acid sequence of an antibody VH variable domain of a said selected binding member may be provided in isolated form, as may a binding member comprising such a VH domain.

Ability to bind the A-FN or the ED-A of fibronectin or other target antigen or isoform may be further tested, e.g. ability to compete with e.g. any one of anti-ED-A antibodies H1, B2, C5, D5, E5, C8, F8, F1, B7, E8 or G9 for binding to the A-FN or a fragment of the A-FN, e.g. the ED-A of fibronectin.

A binding member for use in the invention may bind the A-FN and/or the ED-A of fibronectin specifically. A binding member of the present invention may bind the A-FN and/or the ED-A of fibronectin with the same affinity as anti-ED-A antibody H1, B2, C5, D5, E5, C8, F8, F1, B7, E8 or G9, e.g.

in scFv format, or with an affinity that is better. A binding member for use in the invention may bind the A-FN and/or the ED-A of fibronectin with a $K_D$ of $3\times10^{-8}$ M or an affinity that is better. Preferably, a binding member for use in the invention binds the A-FN and/or the ED-A of fibronectin with a $K_D$ of $2\times10^{-8}$ M or an affinity that is better. More preferably, a binding member for use in the invention binds the A-FN and/or the ED-A of fibronectin with a $K_D$ of $1.7\times10^{-8}$ M or an affinity that is better. Yet more preferably, a binding member for use in the invention binds the A-FN and/or the ED-A of fibronectin with a $K_D$ of $1.4\times10^{-8}$ M or an affinity that is better. Most preferably, a binding member for use in the invention binds the A-FN and/or the ED-A of fibronectin with a $K_D$ of $3\times10^{-9}$ M or an affinity that is better.

A binding member of the present invention may bind to the same epitope on A-FN and/or the ED-A of fibronectin as anti-ED-A antibody H1, B2, C5, D5, E5, C8, F8, F1, B7, E8 or G9.

A binding member for use in the invention may not show any significant binding to molecules other than the A-FN and/or the ED-A of fibronectin. In particular the binding member may not bind other isoforms of fibronectin, for example the ED-B isoform and/or the IIICS isoform of fibronectin.

Variants of antibody molecules disclosed herein may be produced and used in the present invention. The techniques required to make substitutions within amino acid sequences of CDRs, antibody VH or VL domains and binding members generally are available in the art.

Variant sequences may be made, with substitutions that may or may not be predicted to have a minimal or beneficial effect on activity, and tested for ability to bind A-FN and/or the ED-A of fibronectin and/or for any other desired property.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), may be less than about 20 alterations, less than about 15 alterations, less than about 10 alterations or less than about 5 alterations, maybe 5, 4, 3, 2 or 1. Alterations may be made in one or more framework regions and/or one or more CDRs. The alterations normally do not result in loss of function, so a binding member comprising a thus-altered amino acid sequence may retain an ability to bind A-FN and/or the ED-A of fibronectin. For example, it may retain the same quantitative binding as a binding member in which the alteration is not made, e.g. as measured in an assay described herein. The binding member comprising a thus-altered amino acid sequence may have an improved ability to bind A-FN and/or the ED-A of fibronectin.

Novel VH or VL regions carrying CDR-derived sequences for use in the invention may be generated using random mutagenesis of one or more selected VH and/or VL genes to generate mutations within the entire variable domain. In some embodiments one or two amino acid substitutions are made within an entire variable domain or set of CDRs. Another method that may be used is to direct mutagenesis to CDR regions of VH or VL genes.

As noted above, a CDR amino acid sequence substantially as set out herein may be carried as a CDR in a human antibody variable domain or a substantial portion thereof. The HCDR3 sequences substantially as set out herein represent embodiments of the present invention and for example each of these may be carried as a HCDR3 in a human heavy chain variable domain or a substantial portion thereof.

Variable domains employed in the invention may be obtained or derived from any germ-line or rearranged human variable domain, or may be a synthetic variable domain based on consensus or actual sequences of known human variable domains. A variable domain can be derived from a non-human antibody. A CDR sequence for use in the invention (e.g. CDR3) may be introduced into a repertoire of variable domains lacking a CDR (e.g. CDR3), using recombinant DNA technology. For example, Marks et al. (1992) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3—derived sequences of the present invention may be shuffled with repertoires of VH or VL domains lacking a CDR3, and the shuffled complete VH or VL domains combined with a cognate VL or VH domain to provide binding members for use in the invention. The repertoire may then be displayed in a suitable host system such as the phage display system of WO92/01047, which is herein incorporated by reference in its entirety, or any of a subsequent large body of literature, including Kay, Winter & McCafferty (1996), so that suitable binding members may be selected. A repertoire may consist of from anything from $10^4$ individual members upwards, for example at least $10^5$, at least $10^6$, at least $10^7$, at least $10^8$, at least $10^9$ or at least $10^{10}$ members.

Similarly, one or more, or all three CDRs may be grafted into a repertoire of VH or VL domains that are then screened for a binding member or binding members for the A-FN and/or the ED-A of fibronectin.

One or more of the HCDR1, HCDR2 and HCDR3 of antibody H1, B2, C5, D5, E5, C8, F8, F1, B7, E8 or G9, or the set of HCDRs may be employed, and/or one or more of the X LCDR1, LCDR2 and LCDR3 of antibody H1, B2, C5, D5, E5, C8, F8, F1, B7, E8 or G9 or the set of LCDRs of antibody H1, B2, C5, D5, E5, C8, F8, F1, B7, E8 or G9 may be employed.

Similarly, other VH and VL domains, sets of CDRs and sets of HCDRs and/or sets of LCDRs disclosed herein may be employed.

The A-FN and/or the ED-A of fibronectin may be used in a screen for binding members, e.g. antibody molecules, for use in the preparation of a medicament for the treatment of rheumatoid arthritis. The screen may a screen of a repertoire as disclosed elsewhere herein.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of binding members of the present invention made by recombinant DNA techniques may result in the introduction of N- or C-terminal residues encoded by linkers introduced to facilitate cloning or other manipulation steps. Other manipulation steps include the introduction of linkers to join variable domains disclosed elsewhere herein to further protein sequences including antibody constant regions, other variable domains (for example in the production of diabodies) or detectable/functional labels as discussed in more detail elsewhere herein.

Although binding members may comprise a pair of VH and VL domains, single binding domains based on either VH or VL domain sequences may also be used in the invention. It is known that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain binding member able to bind A-FN and/or the ED-A of fibronectin. This may be achieved by phage display screening methods using the so-called hierarchical dual combinatorial approach as disclosed in WO92/01047, herein incorporated by reference in its entirety, in which an individual colony containing either an H or L chain clone is used to infect a complete library of clones encoding the other chain (L or H) and the resulting two-chain binding member is selected in accordance with phage display techniques such as those described in that reference. This technique is also disclosed in Marks 1992.

Binding members for use in the present invention may further comprise antibody constant regions or parts thereof, e.g. human antibody constant regions or parts thereof. For example, a VL domain may be attached at its C-terminal end to antibody light chain constant domains including human Cκ or Cλ chains, e.g. Cλ.

Similarly, a binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG4. Any synthetic or other constant region variant that has these properties and stabilizes variable regions is also useful in embodiments of the present invention.

Binding members for use in the invention may be labelled with a detectable or functional label. A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance. Detectable labels may be attached to antibodies for use in the invention using conventional chemistry known in the art.

There are numerous methods by which the label can produce a signal detectable by external means, for example, by visual examination, electromagnetic radiation, heat, and chemical reagents. The label can also be bound to another binding member that binds the antibody for use in the invention, or to a support.

Labelled binding members, e.g. scFv labelled with a detectable label, may be used diagnostically in vivo, ex vivo or in vitro, and/or therapeutically.

For example, radiolabelled binding members (e.g. binding members conjugated to a radioisotope) may be used in radiodiagnosis and radiotherapy. Radioisotopes which may be conjugated to a binding member for use in the invention include isotopes such as $^{94m}$Tc, $^{99m}$Tc, $^{186}$Re, $^{188}$Re, $^{203}$Pb, $^{67}$Ga, $^{68}$Ga, $^{47}$Sc, $^{111}$In, $^{97}$Ru, $^{62}$Cu, $^{64}$Cu, $^{86}$Y, $^{88}$Y, $^{90}$Y, $^{121}$Sn, $^{161}$Tb, $^{153}$Sm, $^{166}$Ho, $^{105}$Rh, $^{177}$Lu, $^{123}$I, $^{124}$I, $^{125}$I and $^{131}$I.

For example, a binding member for use in the invention labelled with a detectable label may be used to detect, diagnose or monitor rheumatoid arthritis in a human or animal.

A binding member of the present invention may be used for the manufacture of a diagnostic product for use in diagnosing rheumatoid arthritis.

The present invention provides a method of detecting or diagnosing rheumatoid arthritis in a human or animal comprising:
(a) administering to the human or animal a binding member of the present invention, for example labelled with a detectable label, which binds the ED-A isoform of fibronectin and/or the ED-A of fibronectin, and
(b) determining the presence or absence of the binding member in neovasculature of the human or animal body;

wherein localisation of the binding member to neovasculature in the human or animal is indicative of the presence of rheumatoid arthritis.

Where the binding member is labelled with a detectable label, the presence or absence of the detectable label may be determined by detecting the label.

A conjugate or fusion between a binding member for use in the invention and a molecule that exerts a biocidal, cytotoxic immunosuppressive or anti-inflammatory effect on target cells in the lesions and an antibody directed against an extracellular matrix component which is present in such lesions may be employed in the present invention. For example, the conjugated molecule may be inter alia interleukin-10, an anti-inflammatory or other drug, a photosensitizer or a radionuclide. Such conjugates may be used therapeutically, e.g. for treatment of rheumatoid arthritis as referred to herein.

Production and use of fusions or conjugates of binding members with biocidal or cytotoxic molecules is described for example in WO01/62298, which is incorporated by reference herein.

The invention provides a method of treating rheumatoid arthritis, the method comprising administering to an individual a therapeutically effective amount of a medicament comprising a binding member for use in the invention.

The binding member may be a conjugate of (i) a molecule which exerts an anti-inflammatory effect on target cells by cellular interaction, an anti-inflammatory molecule, IL-10, TGF beta, or other drug, and (ii) a binding member for the ED-A isoform of fibronectin and/or the ED-A of fibronectin.

The binding member may be a conjugate of (i) a molecule which exerts an immunosuppressive or anti-inflammatory effect and (ii) a binding member for the ED-A isoform of fibronectin and/or the ED-A of fibronectin.

The binding member may be a conjugate of (i) interleukin-10 (IL10) or TGF beta and (ii) a binding member for the ED-A isoform of fibronectin and/or the ED-A of fibronectin. Such a binding member is useful in aspects of the invention disclosed herein relating to treatment of rheumatoid arthritis.

The invention provides the use of a binding member for use in the invention for the preparation of a medicament for the treatment of rheumatoid arthritis.

The binding member may be a conjugated or fused to a molecule that exerts a biocidal, cytotoxic, immunosuppressive or anti-inflammatory effect as described herein. The binding member may be a conjugate of (i) a molecule which exerts a biocidal or cytotoxic effect on target cells by cellular interaction or has an immunosuppressive or anti-inflammatory effect and (ii) a binding member for human fibronectin according to the present invention.

Also described herein is a conjugate of (i) a molecule which exerts a biocidal or cytotoxic effect on target cells by cellular interaction, or an immunosuppressive or anti-inflammatory effect and (ii) a binding member for human fibronectin according for use in the present invention. Such a conjugate preferably comprises a fusion protein comprising the biocidal, cytotoxic, immunosuppressive or anti-inflammatory molecule and a said binding member, or, where the binding member is two-chain or multi-chain, a fusion protein comprising the biocidal, cytotoxic, immunosuppressive or anti-inflammatory molecule and a polypeptide chain component of said binding member. Preferably the binding member is a single-chain polypeptide, e.g. a single-chain antibody molecule, such as scFv.

A fusion protein comprising the immunosuppressive or anti-inflammatory molecule and a single-chain Fv antibody molecule may be used in the invention.

The immunosuppressive or anti-inflammatory molecule that exerts its effect on target cells by cellular interaction, may interact directly with the target cells, may interact with a membrane-bound receptor on the target cell or perturb the electrochemical potential of the cell membrane. In an exemplary preferred embodiment the molecule is IL-10.

As discussed further below, the specific binding member is preferably an antibody or comprises an antibody antigen-binding site. Conveniently, the specific binding member may be a single-chain polypeptide, such as a single-chain antibody. This allows for convenient production of a fusion protein comprising single-chain antibody and immunosuppressive or anti-inflammatory molecule (e.g. interleukin-10 or TGF beta. An antibody antigen-binding site may be provided by means of association of an antibody VH domain and an antibody VL domain in separate polypeptides, e.g. in a complete antibody or in an antibody fragment such as Fab or diabody. Where the specific binding member is a two-chain or multi-chain molecule (e.g. Fab or whole antibody, respectively), the immunosuppressive or anti-inflammatory molecule may be conjugated as a fusion polypeptide with one or more polypeptide chains in the specific binding member.

The binding member may be conjugated with the immunosuppressive or anti-inflammatory molecule by means of a peptide bond, i.e. within a fusion polypeptide comprising said molecule and the specific binding member or a polypeptide chain component thereof (see e.g. Trachsel et al.). Other means for conjugation include chemical conjugation, especially cross-linking using a bifunctional reagent (e.g. employing DOUBLE-REAGENTS™ Cross-linking Reagents Selection Guide, Pierce).

Also described herein is isolated nucleic acid encoding a binding member for use in the present invention. Nucleic acid may include DNA and/or RNA. A nucleic acid may code for a CDR or set of CDRs or VH domain or VL domain or antibody antigen-binding site or antibody molecule, e.g. scFv or IgG, e.g. IgG1, as defined above.

The nucleotide sequences may encode the VH and/or VL domains disclosed herein.

Further described herein are constructs in the form of plasmids, vectors, transcription or expression cassettes which comprise at least one polynucleotide as described above.

A recombinant host cell that comprises one or more constructs as above are also described. A nucleic acid encoding any CDR or set of CDRs or VH domain or VL domain or antibody antigen-binding site or antibody molecule, e.g. scFv or IgG1 or IgG4 as provided, is described, as is a method of production of the encoded product, which method comprises expression from encoding nucleic acid. Expression may conveniently be achieved by culturing under appropriate conditions recombinant host cells containing the nucleic acid. Following production by expression a VH or VL domain, or binding member may be isolated and/or purified using any suitable technique, then used as appropriate.

A nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

A method of production of an antibody VH variable domain, the method including causing expression from encoding nucleic acid is also described. Such a method may comprise culturing host cells under conditions for production of said antibody VH variable domain.

A method of production may comprise a step of isolation and/or purification of the product. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals. The expression of antibodies and antibody fragments in prokaryotic cells is well established in the art. For a review, see for example Plückthun 1991. A common bacterial host is *E. coli.*

Expression in eukaryotic cells in culture is also available to those skilled in the art as an option for production of a binding member for example Chadd & Chamow (2001), Andersen & Krummen (2002), Larrick & Thomas (2001). Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate. For further details see, for example, Sambrook & Russell (2001). Many known techniques and protocols for manipulation of nucleic acid, for example in preparation of nucleic acid constructs, mutagenesis, sequencing, introduction of DNA into cells and gene expression, and analysis of proteins, are described in detail in Ausubel 1999.

A host cell may contain a nucleic acid as described herein. Such a host cell may be in vitro and may be in culture. Such a host cell may be in vivo. In vivo presence of the host cell may allow intracellular expression of a binding member for use in the present invention as "intrabodies" or intracellular antibodies. Intrabodies may be used for gene therapy.

A method comprising introducing a nucleic acid disclosed herein into a host cell is also described. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene. The purification of the expressed product may be achieved by methods known to one of skill in the art.

The nucleic acid may be integrated into the genome (e.g. chromosome) of the host cell. Integration may be promoted by inclusion of sequences that promote recombination with the genome, in accordance with standard techniques.

A method that comprises using a construct as stated above in an expression system in order to express a binding member or polypeptide as above is also described.

Binding members for use in the present invention are designed to be used in methods of diagnosis or treatment in human or animal subjects, e.g. human. Binding members for use in the invention may be used in diagnosis or treatment of rheumatoid arthritis.

Accordingly, the invention provides methods of treatment comprising administration of a binding member as provided, pharmaceutical compositions comprising such a binding member, and use of such a binding member in the manufacture of a medicament for administration, for example in a method of making a medicament or pharmaceutical composition comprising formulating the binding member with a pharmaceutically acceptable excipient. Pharmaceutically acceptable vehicles are well known and will be adapted by the person skilled in the art as a function of the nature and of the mode of administration of the active compound(s) chosen.

Binding members for use in the present invention will usually be administered in the form of a pharmaceutical composition, which may comprise at least one component in addition to the binding member. Thus pharmaceutical compositions according to the present invention, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, inhaled or by injection, e.g. intravenous.

Pharmaceutical compositions for oral administration such as for example nanobodies etc are also envisaged in the present invention. Such oral formulations may be in tablet, capsule, powder, liquid or semi-solid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be employed, as required. Many methods for the preparation of pharmaceutical formulations are known to those skilled in the art. See e.g. Robinson, 1978.

A composition may be administered alone or in combination with other treatments, concurrently or sequentially or as a combined preparation with another therapeutic agent or agents, dependent upon the condition to be treated.

A binding member for use in the present invention may be used as part of a combination therapy in conjunction with an additional medicinal component. Combination treatments may be used to provide significant synergistic effects, particularly the combination of a binding member for use in the present invention with one or more other drugs. A binding member for use in the present invention may be administered concurrently or sequentially or as a combined preparation with another therapeutic agent or agents, for the treatment of one or more of the conditions listed herein.

For example, a binding member for use in the invention may be used in combination with an existing therapeutic agent for the treatment of rheumatoid arthritis.

Existing therapeutic agents for the treatment of rheumatoid arthritis include IL-10, TGFbeta, photosensitizers and cytotoxic drugs.

A binding member for use in the invention and one or more of the above additional medicinal components may be used in the manufacture of a medicament. The medicament may be for separate or combined administration to an individual, and accordingly may comprise the binding member and the additional component as a combined preparation or as separate preparations. Separate preparations may be used to facilitate separate and sequential or simultaneous administration, and allow administration of the components by different routes e.g. oral and parenteral administration.

In accordance with the present invention, compositions provided may be administered to mammals. Administration may be in a "therapeutically effective amount", this being sufficient to show benefit to a patient. Such benefit may be at least amelioration of at least one symptom. Thus "treatment of rheumatoid arthritis" refers to amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of binding member, the method of administration, the scheduling of administration and other factors known to medical practitioners. Prescription of treatment, e.g. decisions on dosage etc, is within the responsibility of general practitioners and other medical doctors, and may depend on the severity of the symptoms and/or progression of a disease being treated. Appropriate doses of antibody are well known in the art (Ledermann 1991 and Bagshawe 1991. Specific dosages indicated herein, or in the Physician's Desk Reference (2003) as appropriate for the type of medicament being administered, may be used. A therapeutically effective amount or suitable dose of a binding member for use in the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the antibody (e.g. whole antibody, fragment or diabody), and the nature of any detectable label or other molecule attached to the antibody. A typical antibody dose will be in the range 100 μg to 1 g for systemic applications, and 1 μg to 1 mg for topical applications. An initial higher loading dose, followed by one or more lower doses, may be administered. An antibody may be a whole antibody, e.g. the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intravenous administration. In some embodiments of the present invention, treatment is periodic, and the period between administrations is about two weeks or more, e.g. about three weeks or more, about four weeks or more, or about once a month. In other embodiments of the invention, treatment may be given before, and/or after surgery, and may be administered or applied directly at the anatomical site of surgical treatment.

Further aspects and embodiments of the invention will be apparent to those skilled in the art given the present disclosure including the following experimental exemplification.

EXPERIMENTAL

Results
Histochemical Analysis of Human Arthritic Specimens

Expression of fibronectin domains EDA and EDB as well as tenascin-C domains A1 and C were investigated by immunohistochemistry on human arthritic specimens using the F8, L19, F16 and G11 antibodies respectively.

In FIG. 1 darker staining indicates expression of the respective antigens (indicated with white arrows). The anti-EDA antibody F8 led to the strongest staining, therefore all further experiments were performed with this antibody.

Figure 2:
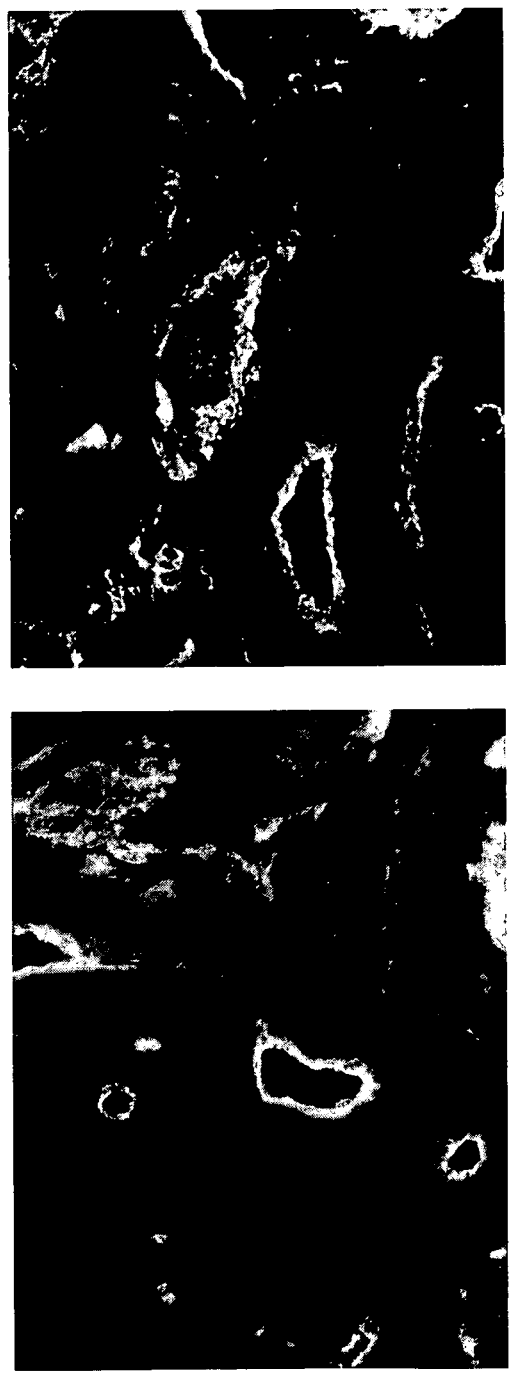
FIG. 2 shows the results of immunofluorescence analysis on human arthritic specimens using the F8 antibody molecule directed against the ED-A domain of fibronectin. White staining indicates strong expression of the antigen.

Immunofluorescence experiments with the F8 antibody were performed which showed a nice perivascular staining (visible as white structures in FIG. 2).

The human monoclonal antibody F8 selectively accumulates at sites of arthritis in mice We studied the in vivo targeting performance of F8 in mini-antibody format (SIP) (Borsi et al. 2002) in the CIA mouse model (Courtney et al. 1980) using both fluorescence and radioactivity for antibody detection. The SIP format consists of a scFv antibody fragment linked to the CH4 domain of human IgE giving rise to a homodimeric protein of 80 kDa in size.

Arthritic mice were injected with SIP(F8) labelled with the near-infrared dye Alexa 750. Twenty-four hours after intravenous injection, animals were imaged using an infrared fluorescence imager (Birchler et al., 1999), revealing a strong and selective antibody accumulation in the lesions present in the arthritic limb, visible as white lighting paws, with some grade 2 swelling in front paws of the mice.

Twenty-four hours after intravenous injection of SIP(F8) radioactively labelled with $^{125}$I, mice were sacrificed and paws imaged by autoradiography (phosphorimaging). A preferential accumulation of radioactivity was observed in the inflamed extremities of mice injected with SIP(F8), visible as black staining in autoradiography. One paw showed an arthritic score of 2 (swelling of the whole paw). Another paw was classified as grade 1 arthritis (swelling of single fingers).

Activity of Anti-Ed-A Antibody-Interleukin-10 Fusion

Figure 8:
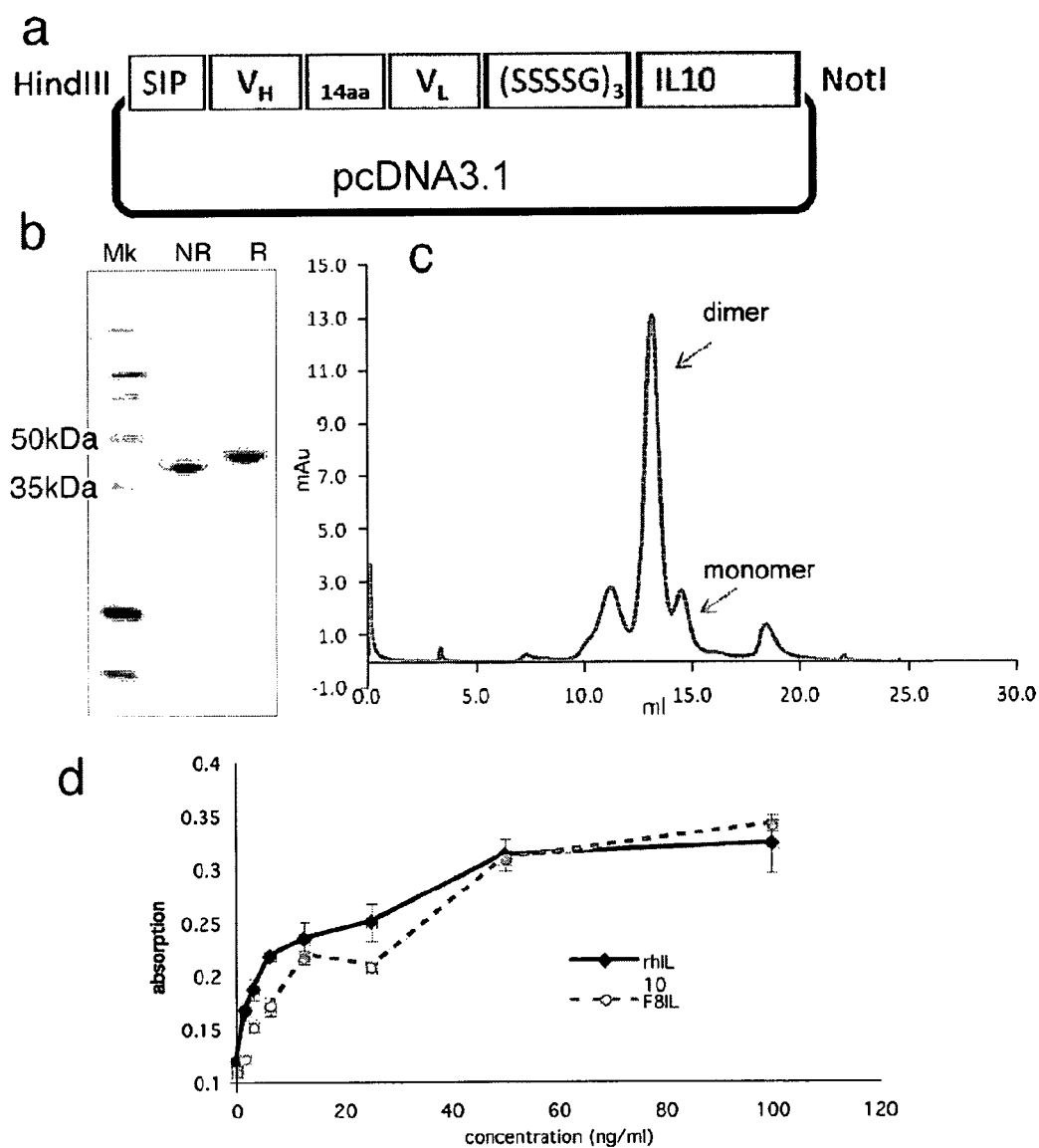
FIG. 8 illustrates cloning, expression and purification of F8-IL10 and HyHel10-IL10.

Antibody molecule F8 in scFv format was conjugated within a fusion protein with interleukin-10 (IL-10). Biological activity of the fusion protein was compared with that of human IL-10 in an assay determining ability to induce IL-4 dependent proliferation of MC/9 cells (Thompson et al., 1991). The results are shown in FIG. 8(d).

Materials and Methods
Immunohistochemical Analysis on Human Arthritic Specimens

Frozen sections of human arthritic specimens were fixed in ice-cold acetone for 10', blocked with Fetal Bovine Serum for 30' and stained for markers of neovasculature (Fibronectin ED-A and ED-B, Tenascin-C domain A1 and C). The F8, L19, F16 and G11 antibodies were used as myc-tagged scFvs in a concentration of 10 ug/ml and incubated for 1 h. The primary antibodies were coincubated with the anti-myc antibody 9E10 in concentration of 7 ug/ml. As tertiary detection antibody a rabbit anti-mouse IgG antibody (Dako, Denmark) and APAAP Mouse Monoclonal (Dako, Denmark) were used in concentrations of 5 and 50 ug/ml respectively for 1 h each. Fast Red Tablets (Sigma, Switzerland) were used to develop the staining incubating for 15'. Slides were counterstained with hematoxylin for 2', washed with water, mounted with Glycergel mounting medium (Dako, Denmark) and analyzed with a Axiovert S100 TV microscope (Zeiss, Switzerland).

Immunofluorescence Analysis on Human Arthritic Specimens

Frozen sections of human arthritic specimens were fixed in ice-cold acetone for 10', blocked with Fetal Bovine Serum for 30' and stained for the EDA domain of fibronectin. The F8 antibody was used as a myc-tagged scFv in a concentration of 10 ug/ml and incubated for 1 h. The primary antibody was coincubated with the anti-myc antibody 9E10 in a concentration of 7 ug/ml. As tertiary detection antibody a fluorescent anti-mouse-Alexa 596 antibody (Molecular Probes, Denmark) was used in a concentration of 10 ug/ml for 1 h each. Slides were counterstained with Hoechst 33342, mounted with Glycergel mounting medium (Dako, Denmark) and analyzed with a AxioScop 2MOT+ microscope (Zeiss, Switzerland).

Animal Model

Male DBA/1 mice (8-12 weeks old) were immunized by intradermal injection at the base of the tail of 200 μg of bovine type II collagen (MD Biosciences) emulsified with equal volumes of Freund's complete adjuvant (MD Biosciences). 2 weeks after the first immunization the procedure was repeated but incomplete Freund's adjuvant (MD Biosciences) was used to emulsify the collagen. Mice were inspected daily and each mouse that exhibited erythema and/or paw swelling in 1 or more limbs was assigned for imaging or treatment studies.

Arthritis was monitored using 2 disease indices (clinical score and paw swelling). For the clinical score each limb was graded daily in a not blinded fashion. (0=normal, 1=swelling of 1 or more fingers of the same limb, 2=swelling of the whole paw), resulting in a maximum possible score of 8 per animal. Paw swelling was assessed every second day using a calliper to measure the thickness of each limb under isoflurane anaesthesia. The mean value of all 4 paws was assigned as paw thickness to each animal.

Near-Infrared-Imaging of Arthritic Paws

The selective accumulation of SIP(F8) in arthritic mice was tested by Near-Infrared-Imaging analysis as described by Birchler et al. (1999). Briefly, purified SIP(F8) was labelled with Alexa750 (MolecularProbes, Leiden, The Netherlands) according to the manufacturer's recommendations and 100 ug of labelled protein were injected into the tail vein of arthritic mice. Mice were anesthetized with Ketamin 80 mg/kg and Medetomidin 0.2 mg/kg and imaged in a near-infrared-mouseimager 24 hr after injection (Trachsel et al. 2007; Birchler et al. 1999).

Biodistribution Experiments

The in vivo targeting performance of SIP(F8) in arthritic mice was evaluated by biodistribution analysis as described before (Borsi et al. 2002; Tarli et al., 1999). Briefly, purified SIP(F8) was radioiodinated and 10 ug of protein, corresponding to 11 uCi $^{125}$I, were injected into the tail vein of arthritic mice. Mice were sacrificed 24 hr after injection and paws were exposed for 1 hour and read in a phosphorimager (Fujifilm BAS-5000) as described before (Trachsel et al. 2007).

Antibodies

The isolation of the anti-ED-B antibody fragment scFv (L19) has been previously described (Pini et al. 1998). The parent anti-ED-A antibody was isolated from the ETH-2 library using published procedures (Giovannoni, Nucleic. Acid Research, 2001, 29(5):E27). The affinity maturation of the parent anti-ED-A antibody, yielding the high affinity anti-ED-A antibodies, is described in the following section.

Affinity Maturation of the Parent Anti-Ed-A Antibody

The parent anti-ED-A antibody (an ETH-2-derived antibody) was used as template for the construction of an affinity maturation library. Sequence variability in the VH CDR1 (DP47 germline) and VL CDR1 (DPK22 germline) of the library was introduced by PCR using partially degenerate primers 5'-CTGGAGCCTGGCGGACCCAGCTCATMNN-MNNMNNGCTAAAGGTGAAT CCAGA-3' (SEQ ID NO: 17) for VH and 5'-CCAGGTTTCTGCTGGTACCAG-GCTAA MNNMNNMNNGCTAACACTCTGACTGGC-CCTGC-3' (SEQ ID NO: 18) for VL (all oligonucleotides were purchased from Operon Biotechnologies, Cologne, Germany), in a process that generates random mutations at positions 31, 32 and 33 of the VH CDR1 and at positions 31, 31a and 32 of the VL CDR1. VHVL combinations were assembled in scFv format by PCR assembly using the primers LMB3 long (5'-CAGGAAACAGCTATGACCAT-GATTAC-3') (SEQ ID NO: 19) and fdseqlong (5'-GACGT-TAGTAAATGAATTTTCTGTATGAGG-3') (SEQ ID NO: 20), using gel-purified VH and VL segments as templates. The assembled VH-VL fragments were doubly digested with NcoI/NotI and cloned into NcoI/NotI-digested pHEN1 phagemid vector (Hoogenboom et al., 1991). The resulting ligation product was electroporated into electrocompetent *E. coli* TG-1 cells according to (Viti et al., 2000), giving rise to a library containing 1.5×10$^7$ individual antibody clones, which was screened for antibodies which bind ED-A with improved affinity.

Selection of Anti-Ed-A Antibodies

The antibody library described above was screened for antibodies which bound ED-A with a greater affinity than the parent anti-ED-A antibody using BIAcore analysis. The antigen (11A12) used in the BIAcore analysis contained the ED-A domain of human fibronectin and has the following amino acid sequence (SEQ ID NO: 120):

MRSYRTEIDKPSQMQVTDVQDNSISVKWLPSSSPVTGYRVTTTPKNGPGP

TKTKTAGPDQTEMTIEGLQPTVEYVVSVYAQNPSGESQPLVQTAVTNIDR

PKGLAFTDVDVDSIKIAWESPQGQVSRYRVTYSSPEDGIHELFPAPDGEE

DTAELQGLRPGSEYTVSVVALHDDMESQPLIGTQSTAIPAPTDLKFTQVT

PTSLSAQWTPPNVQLTGYRVRVTPKEKTGPMKEINLAPDSSSVVVSGLMV

ATKYEVSVYALKDTLTSRPAQGVVTTLENVRSHHHHHH

The nucleotide sequence of antigen (11A12) (SEQ ID NO: 121) is as follows:

atgagatcctaccgaacagaaattgacaaaccatcccagatgcaagtgac cgatgttcaggacaacagcattagtgtcaagtggctgcctt caagttccc ctgttactggttacagagtaaccaccactcccaaaaatggaccaggacca acaaaaactaaaactgcaggtccagatcaaacagaaatgactattgaagg cttgcagcccacagtggagtatgtggttagtgtctatgctcagaatccaa gcggagagagtcagcctctggttcagactgcagtaaccaacattgatcgc cctaaaggactggcattcactgatgtggatgtcgattccatcaaaattgc ttgggaaagcccacaggggcaagtttccaggtacagggtgacctactcga gccctgaggatggaatccatgagctattccctgcacctgatggtgaagaa gacactgcagagctgcaaggcctcagaccgggttctgagtacacagtcag tgtggttgccttgcacgatgatatggagagccagccctgattggaaccc agtccacagctattcctgcaccaactgacctgaagttcactcaggtcaca cccacaagcctgagcgcccagtggacaccacccaatgttcagctcactgg atatcgagtgcgggtgaccccaaggagaagaccggaccaatgaaagaaa tcaaccttgctcctgacagctcatccgtggttgtatcaggacttatggtg gccaccaaatatgaagtgagtgtctatgctcttaaggacactttgacaag cagaccagctcagggagttgtcaccactctggagaatgtcagatctcatc accatcaccatcactaa The nucleotide sequence of the antigen was amplified by PCR using primers containing BamHI and BglII restriction sites at the 5' and 3' respectively. The resulting PCR product and the vector pQE12 (QIAGEN) were digested with BamHI and BglII restriction endonuclease and subsequently ligated in a reaction containing a ratio of insert to vector of 3:1. The resulting vector was sequenced to check that the sequence was correct.

Antigen Preparation

A TG1 electrocompetent Preculture in 10 ml 2TY, Amp, 1% Glucose was electroporated in the presence of 1 µl of a DNA miniprep of 11A12. The pre-culture was then diluted 1:100 (8 ml in 800 ml of 2TY, Amp, 0.1% Glucose) and grown to an OD600 of 0.4-0.6 and then induced with IPTG over night. The following day the cells were spun down and the supernatant filtered (Millipore 0.22 µm). After centrifugation and clarification of the culture broth, 11A12 was purified using a Hitrap column on FPLC. The Ni/column was regenerated as follows: the column was rinsed with 5 column volumes (CV) H2O followed by application of 3CV 0.5 M EDTA/0.2 M Tris pH 8 to wash the old Nickel out from the column. This was followed by rinsing of the column with 5CV H2O. The column was then reloaded with 2CV 100 mM NiSO4 followed by rinsing of the column with several CVs H2O. The column was then equilibrated with 5CV lysis buffer (20 mM imidazol/250 mM NaCl/PBS pH 7.4). The cell lysate was filtered (Millipore 0.45 µm) and loaded onto the column (manually). The column was then put back on FPLC and the lysis buffer left to flow until the UV signal was stable (constant), about 3 CV. The elution program was then started: Gradient from 0% to 100% of Elution Buffer (400 mM imidazol/250 mM NaCl/PBS pH 7.4) in 5CV. The fractions containing the eluted antigen were pooled and dialysed in PBS over night.

Expression and Purification of the Anti-Ed-A Antibodies

The anti-ED-A antibodies were expressed and purified as follows: A TG1 electrocompetent Preculture in 10 ml 2TY, Amp, 1% Glucose was electroporated in the presence of 1 µl of a DNA miniprep of one of the anti-ED-A antibodies. The pre-culture was then diluted 1:100 (8 ml in 800 ml of 2TY, Amp, 0.1% Glucose) and grown to an OD600 of 0.4-0.6 and then induced with IPTG over night. The following day the cells were spun down and the supernatant filtered (Millipore 0.22 µm). The scFv were purified on a Protein A-Sepharose column and Triethylemmine was used to elute the scFvs from the column. The fractions containing the eluted scFvs were dialysed in PBS over night at 4° C. The scFv fractions were then put on a Superdex 75 column with PBS flowing at 0.5 ml/min and 0.25 ml fractions collected. The monomeric fractions were used for BIAcore analysis.

BIAcore™ Analysis 1

The BIAcore™ Chip was flushed overnight at a flow rate of 5 µl/min with HBS-EP buffer BIACORE™, 0.01 M Hepes pH 7.4, 0.15 M NaCl, 3 mM EDTA, 0.005% surfactant P20 (same buffer used for the assay). The antigen (11A12) was diluted to a concentration of 50 µg/ml in acetate buffer (pH 4.0) and the COOH groups on the chip were activated by injection of 50 µl of a mix of N-Hydroxy Succinimmide (NHS) and ethyl-N-(dimethylaminopropyl)-carbodiimide (EDC). 40 µl of the 11A12 antigen were injected onto the chip and the residual free COOH groups were blocked with 30 µl of ethanolamine. After a 0.22 µm filtration, 20 µl of each individual bacterial supernatant were injected onto the chip and interaction with the antigen was monitored in real time.

BIAcore™ Analysis 2

The $k_{on}$, $k_{off}$ and $K_D$ of the parent anti-ED-A antibody and anti-ED-A antibodies B2, C5, D5, C8, F8, B7 and G9 were evaluated using Surface Plasmon Resonance. The chip was equilibrated over night with the same buffer used during the assay at a buffer flow rate of 5 µl/min. The whole coating procedure was performed at this flow rate. The antigen 11A12 was diluted 1:25 with acetate buffer pH 4.00 (provided by BIACORE™) to a final concentration of 20 µg/ml. The NHS and EDC were then mixed and 50 µl injected to activate the COOH groups on the CM5 chip. This was followed by injection of 40 µl of the antigen (this lasts about 40"). Then 30 µl of Ethanolammine were injected in order to block the reactivity of eventual free COOH.

Each sample was assayed at a flow rate 20 µl/min. 20 µl of undiluted monomeric protein (as it comes out from the gel filtration) was injected. The dissociation time was left to run for about 200". Then 10 µl of HCl 10 mM was injected to regenerate the chip. The injection of monomeric protein was repeated at different dilutions, i.e. 1:2 dilution (in PBS) followed by regeneration with HCl. This was followed by a third injection of the protein, at a dilution of 1:4 followed again by regenartion with HCl. The $k_{on}$, $k_{off}$ and KD values for each anti-ED-A antibody were evaluated using the BIAevaluation software.

Selection of Anti-Ed-A Antibodies

BIAcore™ Analysis 1

The BIAcore™ analysis produced a graph for each anti-ED-A antibody which was analysed to deduce the affinity of an antibody for the antigen as follows: The x axis of each graph corresponds to time and the y axis corresponds to Resonance Units (a measure which indicates the binding affinity of the tested antibody for the antigen coated onto the BIAcore™ chip). Each graph showed 3 peaks and 1 dip which correspond to changes of buffer and are therefore irrelevant for the interpretation of the results.

The ascending part of each graph represents the association phase. The steeper is the curve in this part of the graph, the faster is the association of the antibody with the antigen. The descending part of each graph represents the dissociation phase of the antibody from the antigen. The flatter the curve in this part of the graph is, the slower is the dissociation of the antibody from the antigen.

Anti-ED-A antibodies H1, B2, C5, D5, E5, C8, F8, F1, B7, E8 and G9 all showed a flatter dissociation curve than the parent anti-ED-A antibody from which they were derived, indicating that they bind ED-A, and hence also A-FN, with a greater affinity than the parent anti-ED-A antibody. The graphs for antibodies E5, F1, F8 and H1 showed the flattest dissociation curves of all the anti-ED-A antibodies tested. The association curves of antibodies H1, C5, D5, E5, C8, F8 and F1 were flatter than that observed for the parent anti-ED-A antibody while the association curve observed for antibodies B2, B7, E8 and G9 was as steep as the association curve observed for the parent anti-ED-A antibody. However, as bacterial supernatants of IPTG-induced *E. coli* TG-1 cells were used for the BIAcore™ analysis of antibodies H1, B2, C5, D5, E5, C8, F8, F1, B7, E8 and G9, the concentration of the tested antibody samples was unknown but most probably lower than the concentration of the parent anti-ED-A antibody sample used for comparison. Consequently, the association curve of antibodies H1, B2, C5, D5, E5, C8, F8, F1, B7, E8 and G9 may be artificially low due to the low concentration of antibody in the samples used for the BIAcore™ analysis. However, as concentration does not significantly affect the dissociation of an antibody from its target antigen in BIAcore™ analysis, the flat dissociation curves observed for antibodies H1, B2, C5, D5, E5, C8, F8, F1, B7, E8 and G9 show that these antibodies bind ED-A with at least an equal, and probably a higher affinity, than the parent anti-ED-A antibody.

BIAcore Analysis 2

The $k_{on}$, $k_{off}$ and KD values for each anti-ED-A antibody were evaluated using the BIAevaluation software. The $k_{on}$, $k_{off}$ and KD values of the parent anti-ED-A antibody and anti-ED-A antibodies B2, C5, D5, C8, F8, B7 and G9 for antigen 11A12 are detailed in Table 2. Anti-ED-A antibodies B2, C5, D5, C8, F8, B7 and G9 all have a better $K_D$ values for antigen 11A12 than the parent anti-ED-A antibody from which they were derived, indicating that they bind ED-A, and hence also A-FN, with a greater affinity than the parent anti-ED-A antibody.

Sequences

Anti-ED-A antibodies H1, B2, C5, D5, E5, C8, F8, F1, B7, E8 and G9 are all scFv antibodies and were sequenced using conventional methods. The nucleotide sequence of the anti-ED-A antibody H1 is shown in FIG. 4. The amino acid sequence of the anti-ED-A antibody H1 is shown in FIG. 5.

Preferred nucleotide sequences encoding VH and/or VL of anti-ED-A antibodies B2, C5, D5, E5, C8, F8, F1, B7, E8 and G9 are identical to nucleotide sequences encoding VH and/or VL of anti-ED-A antibody H1, except that the nucleotide sequences encoding the H1 CDR1s of the light (VL) and heavy (VH) chain are substituted with the nucleotide sequences encoding the light (VL) and heavy (VH) chain CDR1s listed in Table 1 for the respective antibody.

The preferred nucleotide sequences encoding the VH and/or VL of anti-ED-A scFv F8 diabody are identical to the nucleotide sequences encoding VH and/or VL of anti-ED-A antibody H1, except that the nucleotide sequences encoding the H1 CDR1s of the light (VL) and heavy (VH) chain are substituted with the nucleotide sequences encoding the light (VL) and heavy (VH) chain CDR1s listed in Table 1 for anti-ED-A antibody F8. The preferred nucleotide sequence encoding the linker linking the VH and VL of the anti-ED-A scFv F8 diabody is gggtccagtggcggt (SEQ ID NO: 29).

Anti-ED-A antibodies B2, C5, D5, E5, C8, F8, F1, B7, E8 and G9 have identical amino acid sequences to anti-ED-A antibody H1, except that the amino acid sequences of the H1 CDR1s of the light (VL) and heavy (VH) chain are substituted with the amino acid sequences of the light (VL) and heavy (VH) chain CDR1s listed in Table 1 for the respective antibody. The amino acid sequence of the anti-ED-A scFv F8 diabody is identical to the amino acid sequences of anti-ED-A antibody H1, except that the amino acid sequences of the H1 CDR1s of the light (VL) and heavy (VH) chain are substituted with the amino acid sequences of the light (VL) and heavy (VH) chain CDR1s listed in Table 1 for anti-ED-A antibody F8, and the amino acid sequence of the linker in H1 is substituted with the linker amino acid sequence GSSGG (SEQ ID NO: 28).

The amino acid sequence of the anti-ED-A antibody B2 VH domain (SEQ ID NO: 21) is identical to the amino acid sequence of the VH domain of anti-ED-A antibody H1 except that SEQ ID NO: 23 is substituted for the VH CDR1 of H1.

The amino acid sequence of the anti-ED-A antibody C5 VH domain (SEQ ID NO: 41) is identical to the amino acid sequence of the VH domain of anti-ED-A antibody H1 except that SEQ ID NO: 43 is substituted for the VH CDR1 of H1.

The amino acid sequence of the anti-ED-A antibody D5 VH domain (SEQ ID NO: 51) is identical to the amino acid sequence of the VH domain of anti-ED-A antibody H1 except that SEQ ID NO: 53 is substituted for the VH CDR1 of H1.

The amino acid sequence of the anti-ED-A antibody E5 VH domain (SEQ ID NO: 61) is identical to the amino acid sequence of the VH domain of anti-ED-A antibody H1 except that SEQ ID NO: 63 is substituted for the VH CDR1 of H1.

The amino acid sequence of the anti-ED-A antibody C8 VH domain (SEQ ID NO: 71) is identical to the amino acid sequence of the VH domain of anti-ED-A antibody H1 except that SEQ ID NO: 73 is substituted for the VH CDR1 of H1.

The amino acid sequence of the anti-ED-A antibody F8 VH domain (SEQ ID NO: 81) is identical to the amino acid sequence of the VH domain of anti-ED-A antibody H1 except that SEQ ID NO: 83 is substituted for the VH CDR1 of H1. The VH domain of the anti-ED-A F8 diabody has the same amino acid sequence as VH domain of the anti-ED-A antibody F8 (i.e. SEQ ID NO: 81).

The amino acid sequence of the anti-ED-A antibody F1 VH domain (SEQ ID NO: 91) is identical to the amino acid sequence of the VH domain of anti-ED-A antibody H1 except that SEQ ID NO: 93 is substituted for the VH CDR1 of H1.

The amino acid sequence of the anti-ED-A antibody B7 VH domain (SEQ ID NO: 101) is identical to the amino acid sequence of the VH domain of anti-ED-A antibody H1 except that SEQ ID NO: 103 is substituted for the VH CDR1 of H1.

The amino acid sequence of the anti-ED-A antibody E8 VH domain (SEQ ID NO: 111) is identical to the amino acid sequence of the VH domain of anti-ED-A antibody H1 except that SEQ ID NO: 113 is substituted for the VH CDR1 of H1.

The amino acid sequence of the anti-ED-A antibody G9 VH domain (SEQ ID NO: 31) is identical to the amino acid sequence of the VH domain of anti-ED-A antibody H1 except that SEQ ID NO: 33 is substituted for the VH CDR1 of H1.

The amino acid sequence of the anti-ED-A antibody B2 VL domain (SEQ ID NO: 22) is identical to the amino acid sequence of the VL domain of anti-ED-A antibody H1 except that SEQ ID NO: 26 is substituted for the VL CDR1 of H1.

The amino acid sequence of the anti-ED-A antibody C5 VL domain (SEQ ID NO: 42) is identical to the amino acid sequence of the VL domain of anti-ED-A antibody H1 except that SEQ ID NO: 46 is substituted for the VL CDR1 of H1.

The amino acid sequence of the anti-ED-A antibody D5 VL domain (SEQ ID NO: 52) is identical to the amino acid sequence of the VL domain of anti-ED-A antibody H1 except that SEQ ID NO: 56 is substituted for the VL CDR1 of H1.

The amino acid sequence of the anti-ED-A antibody E5 VL domain (SEQ ID NO: 62) is identical to the amino acid sequence of the VL domain of anti-ED-A antibody H1 except that SEQ ID NO: 66 is substituted for the VL CDR1 of H1.

The amino acid sequence of the anti-ED-A antibody C8 VL domain (SEQ ID NO: 72) is identical to the amino acid sequence of the VL domain of anti-ED-A antibody H1 except that SEQ ID NO: 76 is substituted for the VL CDR1 of H1.

The amino acid sequence of the anti-ED-A antibody F8 VL domain (SEQ ID NO: 82) is identical to the amino acid sequence of the VL domain of anti-ED-A antibody H1 except that SEQ ID NO: 86 is substituted for the VL CDR1 of H1. The VL domain of the anti-ED-A F8 diabody has the same amino acid sequence as VL domain of the anti-ED-A antibody F8 (i.e. SEQ ID NO: 82).

The amino acid sequence of the anti-ED-A antibody F1 VL domain (SEQ ID NO: 92) is identical to the amino acid sequence of the VL domain of anti-ED-A antibody H1 except that SEQ ID NO: 96 is substituted for the VL CDR1 of H1.

The amino acid sequence of the anti-ED-A antibody B7 VL domain (SEQ ID NO: 102) is identical to the amino acid sequence of the VL domain of anti-ED-A antibody H1 except that SEQ ID NO: 106 is substituted for the VL CDR1 of H1.

The amino acid sequence of the anti-ED-A antibody E8 VL domain (SEQ ID NO: 112) is identical to the amino acid sequence of the VL domain of anti-ED-A antibody H1 except that SEQ ID NO: 116 is substituted for the VL CDR1 of H1.

The amino acid sequence of the anti-ED-A antibody G9 VL domain (SEQ ID NO: 32) is identical to the amino acid sequence of the VL domain of anti-ED-A antibody H1 except that SEQ ID NO: 36 is substituted for the VL CDR1 of H1.

Optionally, the amino acid at position 5 of the VH domain of anti-ED-A antibodies H1, B2, C5, D5, E5, C8, F8, F1, B7, E8, G9 and the scFv F8 diabody may be a leucine residue (L) rather than a valine residue (V) as shown in FIG. 4A. In addition, or alternatively, the amino acid at position 18 of the VL domain of anti-ED-A antibodies H1, B2, C5, D5, E5, C8, F8, F1, B7, E8, G9 and the scFv F8 diabody may be an arginine residue (R) rather than a lysine residue (K) as shown in FIG. 4C.

Cloning, Production and Characterization of F8-IL10

The human IL-10 gene was amplified by PCR using the following primer sequences:

```
a backward antisense primer,
                                        (SEQ ID NO: 144)
5'-TCGGGTAGTAGCTCTTCCGGCTCATCGTCCAGCGGCAGCCCAGGCCA GGGCACC-3';
and a forward sense primer,
                                        (SEQ ID NO: 145)
5'-TTTTCCTTTTGCGGCCGCtcattaGTTTCGTATCTTCATTGTCATGT

A-3',
``` which appended part of a 15 amino acid linker (SSSSG)3 (amino acids 243-257 of SEQ ID NO: 149) at its N-terminal and stop codon and NotI restriction site at its C-terminal.

DNA encoding the single-chain variable fragment (F8) was amplified with a signal peptide using the following primer pairs:

```
a backward antisense primer,
                                        (SEQ ID NO: 146)
5'-CCCAAGCTTGTCGACCATGGGCTGGAGCC-3'
and a forward sense primer,
                                        (SEQ ID NO: 147)
5'-GAGCCGGAAGAGCTACTACCCGATGAGGAAGAGAATTCTTTGATTTC

CACCTTGGTCCCTTG-3'.
```

Using this strategy, a HindIII restriction site was inserted at the N-terminal and a complementary part of the linker sequence was inserted at the C-terminal.

The single-chain Fv and IL-10 fragments were then assembled using PCR and cloned into the HindIII and NotI restriction sites of the mammalian cell-expression vector pcDNA3.1(+).

CHO—S cells were stably transfected with the previously described plasmids and selection was carried out in the presence of G418 (0.5 g/l).

Clones of G418-resistant cells were screened for expression of the fusion protein by ELISA using a recombinant EDA of human fibronectin as antigens and Protein A for detection.

The fusion proteins were purified from the cell-culture medium by affinity chromatography over Protein A columns.

The size of the fusion proteins was analysed in reducing and nonreducing conditions on SDS-PAGE and in native conditions by FPLC gel filtration on a Superdex S-200 exclusion column (Amersham Pharmacia Biotech, Dübendorf, Switzerland).

Activity Assay

Biological activity of hIL10 was determined by its ability to induce the IL-4 dependent proliferation of MC/9 cells (Thompson-et al., 1991) using the colorimetric MTT dye-reduction assay. 10.000 MC/9 (ATCC, Manassas, USA) cells/well in 200 μl of medium containing 5 pg (0.05 Units) of murine IL4/ml (eBiosciences) in a 96-well microtiter plate were treated for 48 hr with varying amounts of human IL10. The hIL10 standard and the F8-IL10 fusion protein were used at a maximum of 100 ng/ml IL10 equivalents and serially diluted. 10 μl of 5 mg/ml MTT (Sigma) was added and incubated for 3-5 hr. The cells were then centrifuged, lysed with DMSO and read for absorbance at 570 nm.

REFERENCES

All references cited anywhere in this specification, including those cited anywhere above, are hereby incorporated by reference in their entirety and for all purposes.

Amit et al. (1986), Science, 233:747-753.
Andersen et al. (2002) Current Opinion in Biotechnology 13: 117
Ausubel et al. (1999) 4$^{th}$ eds., *Short Protocols in Molecular Biology: A Compendium of Methods from Current Protocols in Molecular Biology*, John Wiley & Sons.
Bagshawe K. D. et al. (1991) Antibody, Immunoconjugates and Radiopharmaceuticals 4: 915-922
Balza et al. (1988), *FEBS Lett.*, 228: 42-44.
Batista et al. J. Exp. Med., 184: 2197-205, 1996.
Berndt et al. *Histochem Cell Biol* 1998, 109(3):249-255.
Birchler et al. (1999), J. Immunol. Methods, 231, 239-248.
Bird et al. (1988) Science, 242, 423-426
Borsi et al. (1987), J. Cell. Biol., 104, 595-600.
Borsi et al. (1990), *FEBS Lett.*, 261: 175-178.
Borsi et al. (1995), J. Biol. Chem., 270: 6243-6245.
Borsi et al. (1998), Exp. Cell Res., 240, 244-251.
Borsi et al. (2000) *Int J Cancer,* 102(1):75-85.
Brack et al. (2006), Clin. Cancer Res., 12, 3200-3208.
Carnemolla et al. (1989), J. Cell. Biol., 108: 1139-1148.
Caton et al. (1990), J. Immunol., 144:1965-1968.
Chadd et al. (2001), Current Opinion in Biotechnology 12: 188-194
Chothia et al. (1987), J. Mol. Biol., 196:901-917.
Chothia et al. (1989), Nature, 342:877-883.
Courtney et al. (1980) Nature, 14; 283(5748):666-8.
Devos et al. (1983), Nucl. Acids Res. 11: 4307-4323.
ffrench-Constant (1995), Exp. Cell Res., 221, 261-271.
Giovannoni, Nucleic. Acid Research, 2001, 29(5):E27.
Glennie M J et al., 1987 J. Immunol. 139, 2367-2375
Haan et al. (2004), BioCentury, 12(5): A1-A6.
Hanahan et al. (2000), Cell 100, 57-70.
Harlow and Lane, Antibodies: A Laboratory Manual, Cold Spring Harbor Laboratory, Cold Spring Harbor N.Y., pp. 726, 1988
Heikinheimo et al. (1991), Virchows Arch. B Cell Pathol. Incl. Mol. Pathol., 61, 101-109.
Holliger and Bohlen 1999 Cancer and metastasis rev. 18: 411-419.
Holliger et al. (1993a), Proc. Natl. Acad. Sci. USA 90 6444-6448.
Holliger et al. (1993b), Current Opinion Biotechnol 4, 446-449.
Holt et al. (2003) Trends in Biotechnology 21, 484-490.
Hoogenboom et al. (1991), Nucleic Acids Res., 19 (15) 4133-7.
Hu et al. (1996), Cancer Res., 56, 3055-3061.
Huston et al. (1988) PNAS USA, 85, 5879-5883.
Hynes, R. O. (1990). Fibronectins (New York: Springer-Verlag).
Jacobs et al. (2002), Hum. Pathol., 33, 29-38.

Kabat et al. (1987) Sequences of Proteins of Immunological Interest. 4th Edition. US Department of Health and Human Services.
Kabat et al. (1991a), Sequences of Proteins of Immunological Interest, 5th Edition. US Department of Health and Human Services, Public Service, NIH, Washington. (a)
Kabat et al. (1991b), J. Immunol., 147:1709-1719.
Kaspar et al. (2006), Int. J. Cancer, 118, 1331-1339.
Knappik et al., (2000) J. Mol. Biol. 296, 57-86.
Koch et al. *Ann Rheum Dis* 2003, 62 Suppl 2:ii60-67.
Kohler and Milstein, Nature, 256:495-497, 1975
Koide et al. (1998), Journal of Molecular Biology, 284: 1141-1151.
Kontermann et al. (2001), S, *Antibody Engineering*, Springer-Verlag New York, LLC; ISBN: 3540413545.
Kornblihtt et al. (1984), Nucleic Acids Res. 12, 5853-5868.
Koukoulis et al. (1993), J. Submicrosc. Cytol. Pathol., 25, 285-295.
Koukoulis et al. (1995), Ultrastruct. Pathol., 19, 37-43.
Krebs et al. (2001), Journal of Immunological Methods, 254 67-84.
Kriegsmann et al. (2004) *Rheumatol Int,* 24(1):25-33.
Larrick J W and Thomas D W (2001) Current Opinion in Biotechnology 12:411-418.
Ledermann J. A. et al. (1991) Int. J. Cancer 47: 659-664
Li et al. Protein Engineering, 10: 731-736, 1997
Lohi et al. (1995), Int. J. Cancer, 63, 442-449.
Maeda et al. (1983) Biochem. Biophys. Res. Comm. 115: 1040-1047;
Matsumoto et al. (1999), Jpn. J. Cancer Res., 90, 320-325.
McCafferty et al., (1990) Nature, 348, 552-554.
Mendez, M. et al., (1997) Nature Genet, 15(2): 146-156.
Merchand et al., 1998 Nature Biotech. 16:677-681
Neri, D., and Bicknell, R. (2005), Nat Rev Cancer 5, 436-446.
Nygren et al. (1997), Current Opinion in Structural Biology, 7: 463-469.
Oyama et al. (1989), J. Biol. Chem., 264, 10331-10334.
Paolella et al. (1988), Nucleic Acids Res. 16, 3545-3557.
Pini et al. (1998), J. Biol. Chem., 273, 21769-21776.
Plückthun (1991), Bio/Technology 9: 545-551.
Reiter et al. (1996), Nature Biotech, 14, 1239-1245.
Repp et al., 1995 J. Hemat. 377-382.
Ridgeway et al. (1996), Protein Eng., 9, 616-621.
Robinson ed., Sustained and Controlled Release Drug Delivery Systems, Marcel Dekker, Inc., New York, 1978
Roesli et al. (2006), Nature Protocols, 1, 192-199.
Ruf et al. (1991) J. Biol. Chem. 226: 15719-15725.
Rybak et al. (2005), Nat. Methods, 2, 291-298.
Rybak et al. (2006), ChemMedChem., 2, 22-40.
Sambrook and Russell, *Molecular Cloning: a Laboratory Manual:* 3rd edition, 2001, Cold Spring Harbor Laboratory Press
Scarpati et al. (1987) Biochemistry 26: 5234-5238.
Scarpino et al. (1999) J. Pathol. 188, 163-167.
Scheurer et al. (2005), Proteomics 5, 3035-3039.
Segal et al. (1974), PNAS, 71:4298-4302.
Sharon et al. (1990a), PNAS, 87:4814-4817.
Sharon et al. (1990b), J. Immunol., 144:4863-4869.
Silacci et al. (2003), Proteomics, 5, 2340-2350.
Staerz U. D. and Bevan M. J. 1986 PNAS 83
Suresh et al. (1986) Method Enzymol. 121: 210-228
Taniguchi et al. (1983) Nature 302, 305-310;
Tarli et al. *Blood* 1999, 94(1):192-198.
Tavian et al. (1994), Int. J. Cancer, 56, 820-825.
Taylor, *Arthritis Res* 2002, 4 Suppl 3:S99-107.
Terrana et al. (1987), Cancer Res. 47, 3791-3797.
Thompson et al. (1991), J Exp Med, 173:507-510.
Thorpe (2004), Clin. Cancer Res., 10, 415-427.
Trachsel et al. (2006), Adv. Drug Deliv. Rev., 58, 735-754.
Trachsel et al. *Arthritis Res Ther* 2007, 9(1):R9.
Viti et al. (2000), Methods Enzymol., 326, 480-505.
Walsh et al. (1998) *Am J Pathol,* 152(3):691-702.
Ward et al. (1989), Nature 341, 544-546.
Wess In: BioCentury, The Bernstein Report on BioBusiness, 12(42), A1-A7, 2004.

TABLE 1

Nucleotide and amino acid sequences of the heavy chain (VH) and light chain (VL) CDR1s of the anti-ED-A affinity matured antibodies

| Antibody | CDR1 (VH) | CDR1 (VL) |
|---|---|---|
| H1 | CCG CGG AGG<br>P   R   R   (SEQ ID NO: 3) | TCT GCG TGG<br>S   A   W   (SEQ ID NO: 6) |
| B2 | GCG GCT AAG<br>A   A   K   (SEQ ID NO: 23) | GTG GCT TTT<br>V   A   F   (SEQ ID NO: 26) |
| C5 | CCG ATT ACT<br>P   I   T   (SEQ ID NO: 43) | TTG CAT TTT<br>L   H   F   (SEQ ID NO: 46) |
| D5 | GTG ATG AAG<br>V   M   K   (SEQ ID NO: 53) | AAT GCT TTT<br>N   A   F   (SEQ ID NO: 56) |
| E5 | ACT GGT TCT<br>T   G   S   (SEQ ID NO: 63) | CTT GCG CAT<br>L   A   H   (SEQ ID NO: 66) |
| C8 | CTT CAG ACT<br>L   Q   T   (SEQ ID NO: 73) | CTT CCT TTT<br>L   P   F   (SEQ ID NO: 76) |
| F8 | CTG TTT ACG<br>L   F   T   (SEQ ID NO: 83) | ATG CCG TTT<br>M   P   F   (SEQ ID NO: 86) |
| F1 | TAG GCG CGT<br>Q(Amber) A R (SEQ ID NO: 93) | GCG CCT TTT<br>A   P   F   (SEQ ID NO: 96) |
| B7 | CAT TTT GAT<br>H   F   D   (SEQ ID NO: 103) | CTG GCT TTT<br>L   A   F   (SEQ ID NO: 106) |

TABLE 1-continued

Nucleotide and amino acid sequences of the heavy chain (VH) and light chain (VL) CDR1s of the anti-ED-A affinity matured antibodies

| Antibody | CDR1 (VH) | CDR1 (VL) |
|---|---|---|
| E8 | GAT ATG CAT<br>D   M   H (SEQ ID NO: 113) | TCG TCT TTT<br>S   S   F (SEQ ID NO: 116) |
| G9 | CAT ATG CAG<br>H   M   Q (SEQ ID NO: 33) | ACT GCT TTT<br>T   A   F (SEQ ID NO: 36) |

TABLE 2

BIAcore evaluation data

| Antibody | $k_{on}$ (1/Ms) | $k_{off}$ (1/s) | $K_D$ (M) |
|---|---|---|---|
| Parent anti-ED-A antibody | $2.5 \times 10^5$ | 0.02 | $\sim 1 \times 10^{-7}$ |
| B2 | $3.8 \times 10^5$ | $7.54 \times 10^{-3}$ | $\sim 2 \times 10^{-8}$ |
| C5 | $3.04 \times 10^5$ | $9.23 \times 10^{-3}$ | $\sim 3 \times 10^{-8}$ |
| D5 | $4.53 \times 10^5$ | $7.6 \times 10^{-3}$ | $\sim 1.7 \times 10^{-8}$ |
| C8 | $3.8 \times 10^5$ | $5.3 \times 10^{-3}$ | $\sim 1.4 \times 10^{-8}$ |
| F8 | $4.65 \times 10^5$ | $1.4 \times 10^{-3}$ | $\sim 3.1 \times 10^{-9}$ |
| B7 | $2.67 \times 10^5$ | $4.5 \times 10^{-3}$ | $\sim 1.68 \times 10^{-8}$ |
| G9 | $3.6 \times 10^5$ | $7.54 \times 10^{-3}$ | $\sim 2.09 \times 10^{-8}$ |

The invention claimed is:

1. An antibody conjugate comprising an antibody, or an antigen-binding fragment thereof, wherein the antibody or antigen-binding fragment binds the Extra Domain-A (ED-A) of fibronectin and is conjugated to a molecule having anti-inflammatory activity, wherein
said antibody comprises a heavy chain variable (VH) domain and a light chain variable (VL) domain,
said VH domain comprises a set of complementarity determining regions HCDR1, HCDR2 and HCDR3 that comprise the amino acid sequences of SEQ ID NOs: 83, 4, and 5, respectively, and
said VL domain comprises a set of complementarity determining regions LCDR1, LCDR2 and LCDR3 that comprise the amino acid sequences of SEQ ID NOs: 86, 7, and 8, respectively.

2. The antibody conjugate according to claim 1, wherein said VH domain and/or said VL domain comprises a human framework.

3. The antibody conjugate according to claim 1, wherein the VH domain comprises the amino acid sequence of SEQ ID NO: 81; or the amino acid sequence of SEQ ID NO: 81, wherein the amino acid at position 5 of SEQ ID NO: 81 is a leucine residue (L) rather than a valine residue (V).

4. The antibody conjugate according to claim 1, wherein the VL domain comprises the amino acid sequence of SEQ ID NO: 82; or the amino acid sequence of SEQ ID NO: 82, wherein the amino acid at position 18 of SEQ ID NO: 82 is an arginine residue (R) rather than a lysine residue (K).

5. The antibody conjugate according to claim 1, wherein the VH domain comprises the amino acid sequence of SEQ ID NO: 81, wherein the amino acid at position 5 of SEQ ID NO: 81 is a leucine residue (L) rather than a valine residue (V); and the VL domain comprises the amino acid sequence of SEQ ID NO: 82, wherein the amino acid at position 18 of SEQ ID NO: 82 is an arginine residue (R) rather than a lysine residue (K).

6. The antibody conjugate according to claim 5, wherein said antigen-binding fragment comprises a single chain FV (scFv) or is a diabody.

7. The antibody conjugate according to claim 5, wherein said antigen-binding fragment comprises a small immunoprotein (SIP).

8. The antibody conjugate according to claim 5, wherein said antibody or antigen-binding fragment is conjugated to a detectable label.

9. The antibody conjugate according to claim 6, wherein said molecule having anti-inflammatory activity is interleukin-10 (IL-10).

10. The antibody conjugate according to claim 9, wherein said IL-10 is human IL-10.

11. The antibody conjugate according to claim 5, wherein said antibody or antigen-binding fragment is conjugated to said molecule having anti-inflammatory activity via a peptide linker.

12. The antibody conjugate according to claim 11, wherein said peptide linker comprises 15 amino acids.

13. The antibody conjugate according to claim 12, wherein said peptide linker comprises the amino acid sequence (SSSSG)$_3$ (amino acid residues 243-257 of SEQ ID NO: 149).

14. The antibody conjugate according to claim 5, wherein said antigen-binding fragment comprises a scFv or is a diabody, and wherein said VH domain is conjugated to said VL domain via an amino acid linker.

15. The antibody conjugate according to claim 14, wherein said amino acid linker comprises 5 to 25 amino acids.

16. The antibody conjugate according to claim 15, wherein said amino acid linker comprises 5 amino acids.

17. The antibody conjugate according to claim 1, wherein the antibody conjugate comprises:
  (i) the antigen-binding fragment, wherein the antigen-binding fragment comprises a scFv or is a diabody comprising said VH domain and said VL domain, wherein said VH domain is conjugated to said VL domain via a 5 amino acid linker; and
  (ii) human interleukin-10, wherein said VL domain is conjugated to said human interleukin-10 via a peptide linker comprising the amino acid sequence (SSSSG)$_3$ (amino acid residues 243-257 of SEQ ID NO: 149).

18. The antibody conjugate according to claim 1, wherein the antibody conjugate comprises:
  (i) the antigen-binding fragment, wherein the antigen-binding fragment comprises a scFv or is a diabody, wherein the VH domain comprises the amino acid sequence of SEQ ID NO: 81, wherein the amino acid at position 5 of SEQ ID NO: 81 is a leucine residue (L) rather than a valine residue (V); and the VL domain comprises the amino acid sequence of SEQ ID NO: 82, wherein the amino acid at position 18 of SEQ ID NO: 82 is an arginine residue (R) rather than a lysine residue (K);
  wherein said VH domain is conjugated to said VL domain via a 5 amino acid linker; and
  (ii) human interleukin-10, wherein said VL domain is conjugated to said human interleukin-10 via a peptide linker comprising the amino acid sequence (SSSSG)$_3$ (amino acid residues 243-257 of SEQ ID NO: 149).

19. The antibody conjugate according to claim 1, wherein the antibody conjugate consists of:
  (i) the antigen-binding fragment, wherein the antigen-binding fragment is a diabody comprising said VH domain and said VL domain,
  (ii) a 5 amino acid linker, wherein said VH domain is conjugated to said VL domain via the 5 amino acid linker;
  (iii) human interleukin-10; and
  (iv) a peptide linker comprising the amino acid sequence (SSSSG)$_3$ (amino acid residues 243-257 of SEQ ID NO: 149), wherein said VL domain is conjugated to said human interleukin-10 via the peptide linker.

20. A pharmaceutical composition comprising the antibody conjugate according to claim 1 and a pharmaceutically acceptable carrier.

21. The antibody conjugate according to claim 1, wherein the antibody conjugate consists of:
  (i) the antigen-binding fragment, wherein the antigen-binding fragment is a diabody consisting of:
    (a) a VH domain comprising the amino acid sequence of SEQ ID NO: 81, wherein the amino acid at position 5 of SEQ ID NO: 81 is a leucine residue (L) rather than a valine residue (V); and
    (b) a VL domain comprising the amino acid sequence of SEQ ID NO: 82, wherein the amino acid at position 18 of SEQ ID NO: 82 is an arginine residue (R) rather than a lysine residue (K);
  (ii) a 5 amino acid linker, wherein said VH domain is conjugated to said VL domain via the 5 amino acid linker;
  (iii) human interleukin-10; and
  (iv) a peptide linker consisting of the amino acid sequence (SSSSG)$_3$ (amino acid residues 243-257 of SEQ ID NO: 149), wherein said VL domain is conjugated to said human interleukin-10 via the peptide linker.

22. The antibody conjugate according to claim 2, wherein said VH domain comprises a framework from the human germline DP47 gene.

23. The antibody conjugate according to claim 2 or 22, wherein said VL domain comprises a framework from the human germline DPK22 gene.

24. The antibody conjugate according to claim 1, wherein said antibody or antigen-binding fragment comprises a myc-tag sequence.

25. The antibody conjugate according to claim 1, wherein said antibody or antigen-binding fragment is conjugated to a radioisotope.

26. The antibody conjugate according to claim 10, wherein said human IL-10 comprises amino acid residues 258 to 417 of SEQ ID NO: 149.

27. The antibody conjugate according to claim 3, wherein said molecule having anti-inflammatory activity is interleukin-10 (IL-10).

28. The antibody conjugate according to claim 27, wherein said IL-10 is human IL-10.

29. The antibody conjugate according to claim 28, wherein said human IL-10 comprises amino acid residues 258 to 417 of SEQ ID NO: 149.

30. The antibody conjugate according to claim 17, wherein said human IL-10 comprises amino acid residues 258 to 417 of SEQ ID NO: 149.

31. The antibody conjugate according to claim 19, wherein said human IL-10 comprises amino acid residues 258 to 417 of SEQ ID NO: 149.

* * * * *

SEQUENCE LISTING

```
<160> NUMBER OF SEQ ID NOS: 149

<210> SEQ ID NO 1
<211> LENGTH: 118
<212> TYPE: PRT
<213> ORGANISM: Artificial sequence
<220> FEATURE:
<223> OTHER INFORMATION: Synthetic sequence: Amino acid sequence of
      the anti-ED-A antibody H1 heavy chain (VH)

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Arg
            20                  25                  30

Arg Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 2
<211> LENGTH: 125
<212> TYPE: PRT
<213> ORGANISM: Artificial sequence
<220> FEATURE:
<223> OTHER INFORMATION: Synthetic sequence: Amino acid sequence of the
      anti-ED-A antibody H1 light chain (VL)

<400> SEQUENCE: 2

Glu Ile Val Leu Thr Gln Ser Pro Gly Thr Leu Ser Leu Ser Pro Gly
1               5                   10                  15
```

```
Glu Lys Ala Thr Leu Ser Cys Arg Ala Ser Gln Ser Val Ser Ser Ala
            20                  25                  30

Trp Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 3
<211> LENGTH: 3
<212> TYPE: PRT
<213> ORGANISM: Artificial sequence
<220> FEATURE:
<223> OTHER INFORMATION: Synthetic sequence: Amino acid sequence of the
      heavy chain CDR1 of anti-ED-A antibody H1

<400> SEQUENCE: 3

Pro Arg Arg
1

<210> SEQ ID NO 4
<211> LENGTH: 6
<212> TYPE: PRT
<213> ORGANISM: Artificial sequence
<220> FEATURE:
<223> OTHER INFORMATION: Synthetic sequence: Amino acid sequence of the
      heavy chain CDR2 of anti-ED-A antibody H1

<400> SEQUENCE: 4

Ser Gly Ser Gly Gly Ser
1               5

<210> SEQ ID NO 5
<211> LENGTH: 6
<212> TYPE: PRT
<213> ORGANISM: Artificial sequence
<220> FEATURE:
<223> OTHER INFORMATION: Synthetic sequence: Amino acid sequence of the
      heavy chain CDR3 of anti-ED-A antibody H1

<400> SEQUENCE: 5

Ser Thr His Leu Tyr Leu
1               5

<210> SEQ ID NO 6
<211> LENGTH: 3
<212> TYPE: PRT
<213> ORGANISM: Artificial sequence
<220> FEATURE:
<223> OTHER INFORMATION: Synthetic sequence: Amino acid sequence of the
      light chain CDR1 of anti-ED-A antibody H1

<400> SEQUENCE: 6

Ser Ala Trp
1
```

-continued

```
<210> SEQ ID NO 7
<211> LENGTH: 7
<212> TYPE: PRT
<213> ORGANISM: Artificial sequence
<220> FEATURE:
<223> OTHER INFORMATION: Synthetic sequence: Amino acid sequence of the
      light chain CDR2 of anti-ED-A antibody H1

<400> SEQUENCE: 7

Gly Ala Ser Ser Arg Ala Thr
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic sequence: Amino acid sequence of the
      light chain CDR3 of anti-ED-A antibody H1

<400> SEQUENCE: 8

Met Arg Gly Arg Pro Pro
1               5

<210> SEQ ID NO 9

<400> SEQUENCE: 9

000

<210> SEQ ID NO 10

<400> SEQUENCE: 10

000

<210> SEQ ID NO 11
<211> LENGTH: 20
<212> TYPE: PRT
<213> ORGANISM: Artificial sequence
<220> FEATURE:
<223> OTHER INFORMATION: Synthetic sequence: Amino acid sequence of the
      anti-ED-A antibody H1 linker sequence

<400> SEQUENCE: 11

Gly Gly Gly Gly Ser Gly Gly Gly Gly Ser Gly Gly Gly Gly Ser Gly
1               5                   10                  15

Gly Gly Gly Ser
            20

<210> SEQ ID NO 12
<211> LENGTH: 354
<212> TYPE: DNA
<213> ORGANISM: Artificial sequence
<220> FEATURE:
<223> OTHER INFORMATION: Synthetic sequence: Nucleotide sequence of the
      anti-ED-A antibody H1 heavy chain (VH)

<400> SEQUENCE: 12
gaggtgcagc tggtggagtc tgggggaggc ttggtacagc ctggggggtc cctgagactc      60
tcctgtgcag cctctggatt cacctttagc ccgcggagga tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaaagtact     300
```
catttgtatc tttttgacta ctggggccag ggaaccctgg tcaccgtctc gagt    354

<210> SEQ ID NO 13
<211> LENGTH: 387
<212> TYPE: DNA
<213> ORGANISM: Artificial sequence
<220> FEATURE:
<223> OTHER INFORMATION: Synthetic sequence: Nucleotide sequence of the
      anti-ED-A antibody H1 light chain (VL)

<400> SEQUENCE: 13
gaaattgtgt tgacgcagtc tccaggcacc ctgtctttgt ctccagggga aaaagccacc    60
ctctcctgca gggccagtca gagtgttagc tctgcgtggt tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagatgcgtg gtcggccgcc gacgttcggc   300
caagggacca aggtggaaat caaagcggcc gcagaacaaa aactcatctc agaagaggat   360
ctgaatgggg ccgcatagac tgtgaaa                                       387

<210> SEQ ID NO 14
<211> LENGTH: 60
<212> TYPE: DNA
<213> ORGANISM: Artificial sequence
<220> FEATURE:
<223> OTHER INFORMATION: Synthetic sequence: Nucleotide sequence of the
      anti-ED-A antibody H1 linker sequence

<400> SEQUENCE: 14
ggcggtggag gttctggcgg cggtggcagt ggcggtggag gttccggggg tggaggatct    60

<210> SEQ ID NO 15
<211> LENGTH: 17
<212> TYPE: PRT
<213> ORGANISM: Mus musculus

<400> SEQUENCE: 15

Phe Leu Thr Thr Thr Pro Asn Ser Leu Leu Val Ser Trp Gln Ala Pro
1               5                   10                  15

Arg

<210> SEQ ID NO 16
<211> LENGTH: 12
<212> TYPE: PRT
<213> ORGANISM: Mus musculus

<400> SEQUENCE: 16

Ile Ala Trp Glu Ser Pro Gln Gly Gln Val Ser Arg
1               5                   10

<210> SEQ ID NO 17
<211> LENGTH: 52
<212> TYPE: DNA
<213> ORGANISM: Artificial sequence
<220> FEATURE:
<223> OTHER INFORMATION: Synthetic sequence: Partially degenerate primer
<220> FEATURE:
<221> NAME/KEY: misc_feature
<222> LOCATION: (27)..(28)
<223> OTHER INFORMATION: n is a or g or c or t
<220> FEATURE:
<221> NAME/KEY: misc_feature
<222> LOCATION: (30)..(31)
<223> OTHER INFORMATION: n is a or g or c or t

```
<220> FEATURE:
<221> NAME/KEY: misc_feature
<222> LOCATION: (33)..(34)
<223> OTHER INFORMATION: n is a or g or c or t

<400> SEQUENCE: 17
ctggagcctg gcggacccag ctcatmnnmn nmnngctaaa ggtgaatcca ga         52

<210> SEQ ID NO 18
<211> LENGTH: 58
<212> TYPE: DNA
<213> ORGANISM: Artificial sequence
<220> FEATURE:
<223> OTHER INFORMATION: Synthetic sequence: Partially degenerate primer
<220> FEATURE:
<221> NAME/KEY: misc_feature
<222> LOCATION: (28)..(29)
<223> OTHER INFORMATION: n is a or g or c or t
<220> FEATURE:
<221> NAME/KEY: misc_feature
<222> LOCATION: (31)..(32)
<223> OTHER INFORMATION: n is a or g or c or t
<220> FEATURE:
<221> NAME/KEY: misc_feature
<222> LOCATION: (34)..(35)
<223> OTHER INFORMATION: n is a or g or c or t

<400> SEQUENCE: 18
ccaggtttct gctggtacca ggctaamnnm nmnngctaa cactctgact ggccctgc     58

<210> SEQ ID NO 19
<211> LENGTH: 26
<212> TYPE: DNA
<213> ORGANISM: Artificial sequence
<220> FEATURE:
<223> OTHER INFORMATION: Synthetic sequence: Primer LMB3long

<400> SEQUENCE: 19
caggaaacag ctatgaccat gattac                                      26

<210> SEQ ID NO 20
<211> LENGTH: 30
<212> TYPE: DNA
<213> ORGANISM: Artificial sequence
<220> FEATURE:
<223> OTHER INFORMATION: Synthetic sequence: Primer fdseqlong

<400> SEQUENCE: 20
gacgttagta aatgaattt ctgtatgagg                                   30

<210> SEQ ID NO 21
<211> LENGTH: 118
<212> TYPE: PRT
<213> ORGANISM: Artificial sequence
<220> FEATURE:
<223> OTHER INFORMATION: Synthetic sequence: Amino acid sequence of the
      anti-ED-A antibody B2 VH domain

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ala Ala
            20                  25                  30

Lys Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 22
<211> LENGTH: 125
<212> TYPE: PRT
<213> ORGANISM: Artificial sequence
<220> FEATURE:
<223> OTHER INFORMATION: Synthetic sequence: Amino acid sequence of
      the anti-ED-A antibody B2 VL domain

<400> SEQUENCE: 22

Glu Ile Val Leu Thr Gln Ser Pro Gly Thr Leu Ser Leu Ser Pro Gly
 1               5                  10                  15

Glu Lys Ala Thr Leu Ser Cys Arg Ala Ser Gln Ser Val Ser Val Ala
             20                  25                  30

Phe Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                 85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 23
<211> LENGTH: 3
<212> TYPE: PRT
<213> ORGANISM: Artificial sequence
<220> FEATURE:
<223> OTHER INFORMATION: Synthetic sequence: Amino acid sequence of
      the heavy chain CDR1 of anti-ED-A antibody B2

<400> SEQUENCE: 23

Ala Ala Lys
 1

<210> SEQ ID NO 24

<400> SEQUENCE: 24

000

<210> SEQ ID NO 25

<400> SEQUENCE: 25

000

<210> SEQ ID NO 26
<211> LENGTH: 3
```

```
<212> TYPE: PRT
<213> ORGANISM: Artificial sequence
<220> FEATURE:
<223> OTHER INFORMATION: Synthetic sequence: Amino acid sequence of
      the light chain CDR1 of anti-ED-A antibody B2

<400> SEQUENCE: 26

Val Ala Phe
1

<210> SEQ ID NO 27

<400> SEQUENCE: 27

000

<210> SEQ ID NO 28
<211> LENGTH: 5
<212> TYPE: PRT
<213> ORGANISM: Artificial sequence
<220> FEATURE:
<223> OTHER INFORMATION: Synthetic sequence: Linker sequence of F8
      diabody

<400> SEQUENCE: 28

Gly Ser Ser Gly Gly
1               5

<210> SEQ ID NO 29
<211> LENGTH: 15
<212> TYPE: DNA
<213> ORGANISM: Artificial sequence
<220> FEATURE:
<223> OTHER INFORMATION: Synthetic sequence: Linker sequence of F8
      diabody

<400> SEQUENCE: 29
gggtccagtg gcggt                                                15

<210> SEQ ID NO 30

<400> SEQUENCE: 30

000

<210> SEQ ID NO 31
<211> LENGTH: 118
<212> TYPE: PRT
<213> ORGANISM: Artificial sequence
<220> FEATURE:
<223> OTHER INFORMATION: Synthetic sequence: Amino acid sequence of
      the anti-ED-A antibody G9 VH domain

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Met
            20                  25                  30

Gln Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                        85                  90                  95
Ala Lys Ser Thr His Leu Tyr Leu Phe Asp Tyr Trp Gly Gln Gly Thr
                100                 105                 110

Leu Val Thr Val Ser Ser
        115

<210> SEQ ID NO 32
<211> LENGTH: 125
<212> TYPE: PRT
<213> ORGANISM: Artificial sequence
<220> FEATURE:
<223> OTHER INFORMATION: Synthetic sequence: Amino acid sequence of
      the anti-ED-A antibody G9 VL domain

<400> SEQUENCE: 32

Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Thr Ala
                20                  25                  30

Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
                100                 105                 110

Gln Lys Leu Ile Ser Glu Glu Asp Leu Asn Gly Ala Ala
        115                 120                 125

<210> SEQ ID NO 33
<211> LENGTH: 3
<212> TYPE: PRT
<213> ORGANISM: Artificial sequence
<220> FEATURE:
<223> OTHER INFORMATION: Synthetic sequence: Amino acid sequence of
      the heavy chain CDR1 of anti-ED-A antibody G9

<400> SEQUENCE: 33

His Met Gln
1

<210> SEQ ID NO 34

<400> SEQUENCE: 34

000

<210> SEQ ID NO 35

<400> SEQUENCE: 35

000

<210> SEQ ID NO 36
<211> LENGTH: 3
<212> TYPE: PRT
<213> ORGANISM: Artificial sequence
<220> FEATURE:
<223> OTHER INFORMATION: Synthetic sequence: Amino acid sequence of
      the light chain CDR1 of anti-ED-A antibody G9
```

-continued

<400> SEQUENCE: 36

Thr Ala Phe
1

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41
<211> LENGTH: 118
<212> TYPE: PRT
<213> ORGANISM: Artificial sequence
<220> FEATURE:
<223> OTHER INFORMATION: Synthetic sequence: Amino acid sequence of
      the anti-ED-A antibody C5 VH domain

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Pro Ile
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 42
<211> LENGTH: 125
<212> TYPE: PRT
<213> ORGANISM: Artificial sequence
<220> FEATURE:
<223> OTHER INFORMATION: Synthetic sequence: Amino acid sequence of
      the anti-ED-A antibody C5 VL domain

<400> SEQUENCE: 42

```
Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Leu His
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125
```

<210> SEQ ID NO 43
<211> LENGTH: 3
<212> TYPE: PRT
<213> ORGANISM: Artificial sequence
<220> FEATURE:
<223> OTHER INFORMATION: Synthetic sequence: Amino acid sequence of
      the heavy chain CDR1 of anti-ED-A antibody C5

<400> SEQUENCE: 43

Pro Ile Thr
1

<210> SEQ ID NO 44

<400> SEQUENCE: 44

000

<210> SEQ ID NO 45

<400> SEQUENCE: 45

000

<210> SEQ ID NO 46
<211> LENGTH: 3
<212> TYPE: PRT
<213> ORGANISM: Artificial sequence
<220> FEATURE:
<223> OTHER INFORMATION: Synthetic sequence: Amino acid sequence of
      the light chain CDR1 of anti-ED-A antibody C5

<400> SEQUENCE: 46

Leu His Phe
1

<210> SEQ ID NO 47

<400> SEQUENCE: 47

000

<210> SEQ ID NO 48

<400> SEQUENCE: 48

<210> SEQ ID NO 49
<400> SEQUENCE: 49

000

<210> SEQ ID NO 50
<400> SEQUENCE: 50

000

<210> SEQ ID NO 51
<211> LENGTH: 118
<212> TYPE: PRT
<213> ORGANISM: Artificial sequence
<220> FEATURE:
<223> OTHER INFORMATION: Synthetic sequence: Amino acid sequence of
      the anti-ED-A antibody D5 VH domain

<400> SEQUENCE: 51

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Met
            20                  25                  30

Lys Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115
```

<210> SEQ ID NO 52
<211> LENGTH: 125
<212> TYPE: PRT
<213> ORGANISM: Artificial sequence
<220> FEATURE:
<223> OTHER INFORMATION: Synthetic sequence: Amino acid sequence of
      the anti-ED-A antibody D5 VL domain

<400> SEQUENCE: 52

```
Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Asn Ala
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95
```

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 53
<211> LENGTH: 3
<212> TYPE: PRT
<213> ORGANISM: Artificial sequence
<220> FEATURE:
<223> OTHER INFORMATION: Synthetic sequence: Amino acid sequence of
      the heavy chain CDR1 of anti-ED-A antibody D5

<400> SEQUENCE: 53

Val Met Lys
1

<210> SEQ ID NO 54

<400> SEQUENCE: 54

000

<210> SEQ ID NO 55

<400> SEQUENCE: 55

000

<210> SEQ ID NO 56
<211> LENGTH: 3
<212> TYPE: PRT
<213> ORGANISM: Artificial sequence
<220> FEATURE:
<223> OTHER INFORMATION: Synthetic sequence: Amino acid sequence of
      the light chain CDR1 of anti-ED-A antibody D5

<400> SEQUENCE: 56

Asn Ala Phe
1

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

```
<211> LENGTH: 118
<212> TYPE: PRT
<213> ORGANISM: Artificial sequence
<220> FEATURE:
<223> OTHER INFORMATION: Synthetic sequence: Amino acid sequence of
      the anti-ED-A antibody E5 VH domain

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Gly
            20                  25                  30

Ser Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 62
<211> LENGTH: 125
<212> TYPE: PRT
<213> ORGANISM: Artificial sequence
<220> FEATURE:
<223> OTHER INFORMATION: Synthetic sequence: Amino acid sequence of
      the anti-ED-A antibody E5 VL domain

<400> SEQUENCE: 62

Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Leu Ala
            20                  25                  30

His Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 63
<211> LENGTH: 3
<212> TYPE: PRT
<213> ORGANISM: Artificial sequence
<220> FEATURE:
<223> OTHER INFORMATION: Synthetic sequence: Amino acid sequence of
      the heavy chain CDR1 of anti-ED-A antibody E5

<400> SEQUENCE: 63
```

Thr Gly Ser
1

<210> SEQ ID NO 64

<400> SEQUENCE: 64

000

<210> SEQ ID NO 65

<400> SEQUENCE: 65

000

<210> SEQ ID NO 66
<211> LENGTH: 3
<212> TYPE: PRT
<213> ORGANISM: Artificial sequence
<220> FEATURE:
<223> OTHER INFORMATION: Synthetic sequence: Amino acid sequence of
      the light chain CDR1 of anti-ED-A antibody E5

<400> SEQUENCE: 66

Leu Ala His
1

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71
<211> LENGTH: 118
<212> TYPE: PRT
<213> ORGANISM: Artificial sequence
<220> FEATURE:
<223> OTHER INFORMATION: Synthetic sequence: Amino acid sequence of
      the anti-ED-A antibody C8 VH domain

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Leu Gln
            20                  25                  30

Thr Met Ser Trp Val Arg Gln Ala Pro Gly Lys Gly Leu Glu Trp Val
        35                  40                  45

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser
            115

<210> SEQ ID NO 72
<211> LENGTH: 125
<212> TYPE: PRT
<213> ORGANISM: Artificial sequence
<220> FEATURE:
<223> OTHER INFORMATION: Synthetic sequence: Amino acid sequence of
      the anti-ED-A antibody C8 VL domain

<400> SEQUENCE: 72

Glu Ile Val Leu Thr Gln Ser Pro Gly Thr Leu Ser Leu Ser Pro Gly
 1               5                  10                  15

Glu Lys Ala Thr Leu Ser Cys Arg Ala Ser Gln Ser Val Ser Leu Pro
                 20                  25                  30

Phe Leu Ala Trp Tyr Gln Gln Lys Pro Gly Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                 85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
            115                 120                 125

<210> SEQ ID NO 73
<211> LENGTH: 3
<212> TYPE: PRT
<213> ORGANISM: Artificial sequence
<220> FEATURE:
<223> OTHER INFORMATION: Synthetic sequence: Amino acid sequence of
      the heavy chain CDR1 of anti-ED-A antibody C8

<400> SEQUENCE: 73

Leu Gln Thr
 1

<210> SEQ ID NO 74

<400> SEQUENCE: 74

000

<210> SEQ ID NO 75

<400> SEQUENCE: 75

000
```

-continued

<210> SEQ ID NO 76
<211> LENGTH: 3
<212> TYPE: PRT
<213> ORGANISM: Artificial sequence
<220> FEATURE:
<223> OTHER INFORMATION: Synthetic sequence: Amino acid sequence of
      the light chain CDR1 of anti-ED-A antibody C8

<400> SEQUENCE: 76

Leu Pro Phe
1

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81
<211> LENGTH: 118
<212> TYPE: PRT
<213> ORGANISM: Artificial sequence
<220> FEATURE:
<223> OTHER INFORMATION: Synthetic sequence: Amino acid sequence of
      the anti-ED-A antibody F8 VH domain

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 82
<211> LENGTH: 125

-continued

```
<212> TYPE: PRT
<213> ORGANISM: Artificial sequence
<220> FEATURE:
<223> OTHER INFORMATION: Synthetic sequence: Amino acid sequence of
      the anti-ED-A antibody F8 VL domain

<400> SEQUENCE: 82

Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Met Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 83
<211> LENGTH: 3
<212> TYPE: PRT
<213> ORGANISM: Artificial sequence
<220> FEATURE:
<223> OTHER INFORMATION: Synthetic sequence: Amino acid sequence of
      the heavy chain CDR1 of anti-ED-A antibody F8

<400> SEQUENCE: 83

Leu Phe Thr
1

<210> SEQ ID NO 84

<400> SEQUENCE: 84

000

<210> SEQ ID NO 85

<400> SEQUENCE: 85

000

<210> SEQ ID NO 86
<211> LENGTH: 3
<212> TYPE: PRT
<213> ORGANISM: Artificial sequence
<220> FEATURE:
<223> OTHER INFORMATION: Synthetic sequence: Amino acid sequence of
      the light chain CDR1 of anti-ED-A antibody F8

<400> SEQUENCE: 86

Met Pro Phe
1

<210> SEQ ID NO 87

<400> SEQUENCE: 87
```

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91
<211> LENGTH: 118
<212> TYPE: PRT
<213> ORGANISM: Artificial sequence
<220> FEATURE:
<223> OTHER INFORMATION: Synthetic sequence: Amino acid sequence of
      the anti-ED-A antibody F1 VH domain

<400> SEQUENCE: 91

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gln Ala
            20                  25                  30

Arg Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115
```

<210> SEQ ID NO 92
<211> LENGTH: 125
<212> TYPE: PRT
<213> ORGANISM: Artificial sequence
<220> FEATURE:
<223> OTHER INFORMATION: Synthetic sequence: Amino acid sequence of
      the anti-ED-A antibody F1 VL domain

<400> SEQUENCE: 92

```
Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Ala Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
```

```
                 50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                 85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125
```

<210> SEQ ID NO 93
<211> LENGTH: 3
<212> TYPE: PRT
<213> ORGANISM: Artificial sequence
<220> FEATURE:
<223> OTHER INFORMATION: Synthetic sequence: Amino acid sequence of
      the heavy chain CDR1 of anti-ED-A antibody F1

<400> SEQUENCE: 93

Gln Ala Arg
 1

<210> SEQ ID NO 94

<400> SEQUENCE: 94

000

<210> SEQ ID NO 95

<400> SEQUENCE: 95

000

<210> SEQ ID NO 96
<211> LENGTH: 3
<212> TYPE: PRT
<213> ORGANISM: Artificial sequence
<220> FEATURE:
<223> OTHER INFORMATION: Synthetic sequence: Amino acid sequence of
      the light chain CDR1 of anti-ED-A antibody F1

<400> SEQUENCE: 96

Ala Pro Phe
 1

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 118
<212> TYPE: PRT
<213> ORGANISM: Artificial sequence
<220> FEATURE:
<223> OTHER INFORMATION: Synthetic sequence: Amino acid sequence of
      the anti-ED-A antibody B7 VH domain

<400> SEQUENCE: 101

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Phe
            20                  25                  30

Asp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115
```

<210> SEQ ID NO 102
<211> LENGTH: 125
<212> TYPE: PRT
<213> ORGANISM: Artificial sequence
<220> FEATURE:
<223> OTHER INFORMATION: Synthetic sequence: Amino acid sequence of
      the anti-ED-A antibody B7 VL domain

<400> SEQUENCE: 102

```
Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Leu Ala
            20                  25                  30

Phe Leu Ala Trp Tyr Gln Gln Lys Pro Gly Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125
```

<210> SEQ ID NO 103
<211> LENGTH: 3
<212> TYPE: PRT

<213> ORGANISM: Artificial sequence
<220> FEATURE:
<223> OTHER INFORMATION: Synthetic sequence: Amino acid sequence of
      the heavy chain CDR1 of anti-ED-A antibody B7

<400> SEQUENCE: 103

His Phe Asp
1

<210> SEQ ID NO 104

<400> SEQUENCE: 104

000

<210> SEQ ID NO 105

<400> SEQUENCE: 105

000

<210> SEQ ID NO 106
<211> LENGTH: 3
<212> TYPE: PRT
<213> ORGANISM: Artificial sequence
<220> FEATURE:
<223> OTHER INFORMATION: Synthetic sequence: Amino acid sequence of
      the light chain CDR1 of anti-ED-A antibody B7

<400> SEQUENCE: 106

Leu Ala Phe
1

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111
<211> LENGTH: 118
<212> TYPE: PRT
<213> ORGANISM: Artificial sequence
<220> FEATURE:
<223> OTHER INFORMATION: Synthetic sequence: Amino acid sequence of
      the anti-ED-A antibody E8 VH domain

<400> SEQUENCE: 111

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Asp Met
            20                  25                  30

His Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
                100                 105                 110

Leu Val Thr Val Ser Ser
            115

<210> SEQ ID NO 112
<211> LENGTH: 125
<212> TYPE: PRT
<213> ORGANISM: Artificial sequence
<220> FEATURE:
<223> OTHER INFORMATION: Synthetic sequence: Amino acid sequence of
      the anti-ED-A antibody E8 VL domain

<400> SEQUENCE: 112

Glu Ile Val Leu Thr Gln Ser Pro Gly Thr Leu Ser Leu Ser Pro Gly
  1               5                  10                  15

Glu Lys Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                 85                  90                  95

Pro Thr Phe Gly Gln Gly Thr Lys Val Glu Ile Lys Ala Ala Ala Glu
                100                 105                 110

Gln Lys Leu Ile Ser Glu Glu Asp Leu Asn Gly Ala Ala
            115                 120                 125

<210> SEQ ID NO 113
<211> LENGTH: 3
<212> TYPE: PRT
<213> ORGANISM: Artificial sequence
<220> FEATURE:
<223> OTHER INFORMATION: Synthetic sequence: Amino acid sequence of
      the heavy chain CDR1 of anti-ED-A antibody E8

<400> SEQUENCE: 113

Asp Met His
  1

<210> SEQ ID NO 114

<400> SEQUENCE: 114

000
```

<210> SEQ ID NO 115

<400> SEQUENCE: 115

000

<210> SEQ ID NO 116
<211> LENGTH: 3
<212> TYPE: PRT
<213> ORGANISM: Artificial sequence
<220> FEATURE:
<223> OTHER INFORMATION: Synthetic sequence: Amino acid sequence of
      the light chain CDR1 of anti-ED-A antibody E8

<400> SEQUENCE: 116

Ser Ser Phe
1

<210> SEQ ID NO 117

<400> SEQUENCE: 117

000

<210> SEQ ID NO 118
<211> LENGTH: 90
<212> TYPE: PRT
<213> ORGANISM: Homo sapiens

<400> SEQUENCE: 118

Asn Ile Asp Arg Pro Lys Gly Leu Ala Phe Thr Asp Val Asp Val Asp
1               5                   10                  15

Ser Ile Lys Ile Ala Trp Glu Ser Pro Gln Gly Gln Val Ser Arg Tyr
                20                  25                  30

Arg Val Thr Tyr Ser Ser Pro Glu Asp Gly Ile His Glu Leu Phe Pro
            35                  40                  45

Ala Pro Asp Gly Glu Glu Asp Thr Ala Glu Leu Gln Gly Leu Arg Pro
        50                  55                  60

Gly Ser Glu Tyr Thr Val Ser Val Val Ala Leu His Asp Asp Met Glu
65                  70                  75                  80

Ser Gln Pro Leu Ile Gly Thr Gln Ser Thr
                85                  90

<210> SEQ ID NO 119
<211> LENGTH: 90
<212> TYPE: PRT
<213> ORGANISM: Mus musculus

<400> SEQUENCE: 119

Asn Ile Asp Arg Pro Lys Gly Leu Ala Phe Thr Asp Val Asp Val Asp
1               5                   10                  15

Ser Ile Lys Ile Ala Trp Glu Ser Pro Gln Gly Gln Val Ser Arg Tyr
                20                  25                  30

Arg Val Thr Tyr Ser Ser Pro Glu Asp Gly Ile Arg Glu Leu Phe Pro
            35                  40                  45

Ala Pro Asp Gly Glu Asp Asp Thr Ala Glu Leu Gln Gly Leu Arg Pro
        50                  55                  60

Gly Ser Glu Tyr Thr Val Ser Val Val Ala Leu His Asp Asp Met Glu
65                  70                  75                  80

Ser Gln Pro Leu Ile Gly Ile Gln Ser Thr
                85                  90

<210> SEQ ID NO 120
<211> LENGTH: 288
<212> TYPE: PRT
<213> ORGANISM: Artificial sequence
<220> FEATURE:
<223> OTHER INFORMATION: Synthetic sequence: Antigen (11A12) containing the ED-A domain of human fibronectin

<400> SEQUENCE: 120

```
Met Arg Ser Tyr Arg Thr Glu Ile Asp Lys Pro Ser Gln Met Gln Val
1               5                   10                  15

Thr Asp Val Gln Asp Asn Ser Ile Ser Val Lys Trp Leu Pro Ser Ser
            20                  25                  30

Ser Pro Val Thr Gly Tyr Arg Val Thr Thr Pro Lys Asn Gly Pro
        35                  40                  45

Gly Pro Thr Lys Thr Lys Thr Ala Gly Pro Asp Gln Thr Glu Met Thr
    50                  55                  60

Ile Glu Gly Leu Gln Pro Thr Val Glu Tyr Val Val Ser Val Tyr Ala
65                  70                  75                  80

Gln Asn Pro Ser Gly Glu Ser Gln Pro Leu Val Gln Thr Ala Val Thr
                85                  90                  95

Asn Ile Asp Arg Pro Lys Gly Leu Ala Phe Thr Asp Val Asp Val Asp
            100                 105                 110

Ser Ile Lys Ile Ala Trp Glu Ser Pro Gln Gly Gln Val Ser Arg Tyr
        115                 120                 125

Arg Val Thr Tyr Ser Ser Pro Glu Asp Gly Ile His Glu Leu Phe Pro
    130                 135                 140

Ala Pro Asp Gly Glu Glu Asp Thr Ala Glu Leu Gln Gly Leu Arg Pro
145                 150                 155                 160

Gly Ser Glu Tyr Thr Val Ser Val Val Ala Leu His Asp Asp Met Glu
                165                 170                 175

Ser Gln Pro Leu Ile Gly Thr Gln Ser Thr Ala Ile Pro Ala Pro Thr
            180                 185                 190

Asp Leu Lys Phe Thr Gln Val Thr Pro Thr Ser Leu Ser Ala Gln Trp
        195                 200                 205

Thr Pro Pro Asn Val Gln Leu Thr Gly Tyr Arg Val Arg Val Thr Pro
    210                 215                 220

Lys Glu Lys Thr Gly Pro Met Lys Glu Ile Asn Leu Ala Pro Asp Ser
225                 230                 235                 240

Ser Ser Val Val Val Ser Gly Leu Met Val Ala Thr Lys Tyr Glu Val
                245                 250                 255

Ser Val Tyr Ala Leu Lys Asp Thr Leu Thr Ser Arg Pro Ala Gln Gly
            260                 265                 270

Val Val Thr Thr Leu Glu Asn Val Arg Ser His His His His His
        275                 280                 285
```

<210> SEQ ID NO 121
<211> LENGTH: 867
<212> TYPE: DNA
<213> ORGANISM: Artificial sequence
<220> FEATURE:
<223> OTHER INFORMATION: Synthetic sequence: Nucleotide sequence of antigen (11A12)

<400> SEQUENCE: 121

```
atgagatcct accgaacaga aattgacaaa ccatcccaga tgcaagtgac cgatgttcag      60
gacaacagca ttagtgtcaa gtggctgcct tcaagttccc ctgttactgg ttacagagta     120
```

```
accaccactc ccaaaaatgg accaggacca acaaaaacta aaactgcagg tccagatcaa    180
acagaaatga ctattgaagg cttgcagccc acagtggagt atgtggttag tgtctatgct    240
cagaatccaa gcggagagag tcagcctctg gttcagactg cagtaaccaa cattgatcgc    300
cctaaaggac tggcattcac tgatgtggat gtcgattcca tcaaaattgc ttgggaaagc    360
ccacaggggc aagtttccag gtacagggtg acctactcga gccctgagga tggaatccat    420
gagctattcc ctgcacctga tggtgaagaa gacactgcag agctgcaagg cctcagaccg    480
ggttctgagt acacagtcag tgtggttgcc ttgcacgatg atatggagag ccagcccctg    540
attggaaccc agtccacagc tattcctgca ccaactgacc tgaagttcac tcaggtcaca    600
cccacaagcc tgagcgccca gtggacacac ccaatgttc agctcactgg atatcgagtg    660
cgggtgaccc ccaaggagaa gaccggacca atgaaagaaa tcaaccttgc tcctgacagc    720
tcatccgtgg ttgtatcagg acttatggtg gccaccaaat atgaagtgag tgtctatgct    780
cttaaggaca ctttgacaag cagaccagct cagggagttg tcaccactct ggagaatgtc    840
agatctcatc accatcacca tcactaa                                        867
```

```
<210> SEQ ID NO 122
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody H1

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Arg
            20                  25                  30

Arg Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115
```

```
<210> SEQ ID NO 123
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody B2

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Ala
            20                  25                  30
```

```
Lys Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
             100                 105                 110

Leu Val Thr Val Ser Ser
         115

<210> SEQ ID NO 124
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody C5

<400> SEQUENCE: 124

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Pro Ile
             20                  25                  30

Thr Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
             100                 105                 110

Leu Val Thr Val Ser Ser
         115

<210> SEQ ID NO 125
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody D5

<400> SEQUENCE: 125

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Val Met
             20                  25                  30

Lys Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80
```

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 126
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody E5

<400> SEQUENCE: 126

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Gly
            20                  25                  30

Ser Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 127
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody C8

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Gln
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 128
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody F8

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 129
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody F1

<400> SEQUENCE: 129

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Ala
            20                  25                  30

Arg Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 130
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody B7

-continued

<400> SEQUENCE: 130

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Phe
            20                  25                  30

Asp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 131
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody E8

<400> SEQUENCE: 131

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Met
            20                  25                  30

His Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 132
<211> LENGTH: 118
<212> TYPE: PRT
<213> ORGANISM: Artificial sequence
<220> FEATURE:
<223> OTHER INFORMATION: Synthetic sequence: VH domain of anti-ED-A
      antibody G9

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Met
            20                  25                  30

Gln Met Ser Trp Val Arg Gln Ala Pro Gly Lys Gly Leu Glu Trp Val

```
                    35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser
            115

<210> SEQ ID NO 133
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody H1

<400> SEQUENCE: 133

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ala
             20                  25                  30

Trp Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                 85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 134
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody B2

<400> SEQUENCE: 134

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Val Ala
             20                  25                  30

Phe Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
```

```
                  85                  90                  95

Pro Thr Phe Gly Gln Gly Thr Lys Val Glu Ile Lys Ala Ala Ala Glu
                100                 105                 110

Gln Lys Leu Ile Ser Glu Glu Asp Leu Asn Gly Ala Ala
        115                 120                 125

<210> SEQ ID NO 135
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody C5

<400> SEQUENCE: 135

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Leu His
                20                  25                  30

Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
                100                 105                 110

Gln Lys Leu Ile Ser Glu Glu Asp Leu Asn Gly Ala Ala
        115                 120                 125

<210> SEQ ID NO 136
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody D5

<400> SEQUENCE: 136

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ala
                20                  25                  30

Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
                100                 105                 110

Gln Lys Leu Ile Ser Glu Glu Asp Leu Asn Gly Ala Ala
        115                 120                 125
```

```
<210> SEQ ID NO 137
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody E5

<400> SEQUENCE: 137

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Leu Ala
            20                  25                  30

His Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 138
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody C8

<400> SEQUENCE: 138

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Leu Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 139
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody F8

<400> SEQUENCE: 139
```

-continued

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125
```

<210> SEQ ID NO 140
<211> LENGTH: 125
<212> TYPE: PRT
<213> ORGANISM: Artificial sequence
<220> FEATURE:
<223> OTHER INFORMATION: Synthetic sequence: VL domain of anti-ED-A antibody F1

<400> SEQUENCE: 140

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125
```

<210> SEQ ID NO 141
<211> LENGTH: 125
<212> TYPE: PRT
<213> ORGANISM: Artificial sequence
<220> FEATURE:
<223> OTHER INFORMATION: Synthetic sequence: VL domain of anti-ED-A antibody B7

<400> SEQUENCE: 141

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Leu Ala
            20                  25                  30

Phe Leu Ala Trp Tyr Gln Gln Lys Pro Gly Gln Ala Pro Arg Leu Leu
        35                  40                  45
```

```
Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 142
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody E8

<400> SEQUENCE: 142

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 143
<211> LENGTH: 125
<212> TYPE: PRT
<213> ORGANISM: Artificial sequence
<220> FEATURE:
<223> OTHER INFORMATION: Synthetic sequence: VL domain of anti-ED-A
      antibody G9

<400> SEQUENCE: 143

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Thr Ala
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                85                  90                  95
```

```
Pro Thr Phe Gly Gln Gly Thr Lys Val Glu Ile Lys Ala Ala Ala Glu
            100                 105                 110

Gln Lys Leu Ile Ser Glu Glu Asp Leu Asn Gly Ala Ala
        115                 120                 125

<210> SEQ ID NO 144
<211> LENGTH: 54
<212> TYPE: DNA
<213> ORGANISM: Artificial sequence
<220> FEATURE:
<223> OTHER INFORMATION: Synthetic sequence: Primer

<400> SEQUENCE: 144
tcgggtagta gctcttccgg ctcatcgtcc agcggcagcc caggccaggg cacc        54

<210> SEQ ID NO 145
<211> LENGTH: 48
<212> TYPE: DNA
<213> ORGANISM: Artificial sequence
<220> FEATURE:
<223> OTHER INFORMATION: Synthetic sequence: Primer

<400> SEQUENCE: 145
ttttcctttt gcggccgctc attagtttcg tatcttcatt gtcatgta              48

<210> SEQ ID NO 146
<211> LENGTH: 29
<212> TYPE: DNA
<213> ORGANISM: Artificial sequence
<220> FEATURE:
<223> OTHER INFORMATION: Synthetic sequence: Primer

<400> SEQUENCE: 146
cccaagcttg tcgaccatgg gctggagcc                                   29

<210> SEQ ID NO 147
<211> LENGTH: 62
<212> TYPE: DNA
<213> ORGANISM: Artificial sequence
<220> FEATURE:
<223> OTHER INFORMATION: Synthetic sequence: Primer

<400> SEQUENCE: 147
gagccggaag agctactacc cgatgaggaa gagaattctt tgatttccac cttggtccct  60
tg                                                                62

<210> SEQ ID NO 148
<211> LENGTH: 1417
<212> TYPE: DNA
<213> ORGANISM: Artificial Sequence
<220> FEATURE:
<223> OTHER INFORMATION: Synthetic sequence: F8-IL10

<400> SEQUENCE: 148
aagcttgtcg accatgggct ggagcctgat cctcctgttc ctcgtcgctg tggctacagg  60 taagggctc acagtagcag gcttgaggtc tggacatata tatgggtgac aatgacatcc  120
actttgcctt tctctccaca ggtgtgcact cggaggtgca gctgttggag tctgggggag  180
gcttggtaca gcctgggggg tccctgagac tctcctgtgc agcctctgga ttcaccttta  240 gcctgttac gatgagctgg gtccgccagg ctccagggaa ggggctggag tgggtctcag  300
ctattagtgg tagtggtggt agcacatact acgcagactc cgtgaagggc cggttcacca  360
```

```
tctccagaga caattccaag aacacgctgt atctgcaaat gaacagcctg agagccgagg    420
acacggccgt atattactgt gcgaaaagta ctcatttgta tcttttgac tactggggcc    480
agggaaccct ggtcaccgtc tcgagtggtg gaggcggttc aggcggaggt ggctctggcg    540
gtggcggaga aattgtgttg acgcagtctc caggcaccct gtctttgtct ccaggggaaa    600
gagccaccct ctcctgcagg gccagtcaga gtgttagcat gccgttttta gcctggtacc    660
agcagaaacc tggccaggct cccaggctcc tcatctatgg tgcatccagc agggccactg    720
gcatcccaga caggttcagt ggcagtgggt ctgggacaga cttcactctc accatcagca    780
gactggagcc tgaagatttt gcagtgtatt actgtcagca gatgcgtggt cggccgccga    840
cgttcggcca agggaccaag gtggaaatca agaattctc ttcctcatcg gtagtagct    900
cttccggctc atcgtccagc ggcagcccag gccagggcac ccagtctgag aacagctgca    960
cccacttccc aggcaacctg cctaacatgc ttcgagatct ccgagatgcc ttcagcagag   1020
tgaagacttt ctttcaaatg aaggatcagc tggacaactt gttgttaaag gagtccttgc   1080
tggaggactt taagggttac ctgggttgcc aagccttgtc tgagatgatc cagtttttacc   1140
tggaggaggt gatgccccaa gctgagaacc aagacccaga catcaaggcg catgtgaact   1200
ccctggggga gaacctgaag accctcaggc tgaggctacg cgctgtcat cgatttcttc   1260
cctgtgaaaa caagagcaag gccgtggagc aggtgaagaa tgccttaat aagctccaag   1320
agaaaggcat ctacaaagcc atgagtgagt ttgacatctt catcaactac atagaagcct   1380
acatgacaat gaagatacga aactaatgag cggccgc                            1417
```

<210> SEQ ID NO 149
<211> LENGTH: 417
<212> TYPE: PRT
<213> ORGANISM: Artificial Sequence
<220> FEATURE:
<223> OTHER INFORMATION: Synthetic sequence: F8-IL10

<400> SEQUENCE: 149

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Ser Met Pro Phe Leu Ala Trp Tyr Gln Gln Lys Pro Gly Gln Ala
                165                 170                 175
```

-continued

```
Pro Arg Leu Leu Ile Tyr Gly Ala Ser Ser Arg Ala Thr Gly Ile Pro
            180                 185                 190
Asp Arg Phe Ser Gly Ser Gly Ser Gly Thr Asp Phe Thr Leu Thr Ile
        195                 200                 205
Ser Arg Leu Glu Pro Glu Asp Phe Ala Val Tyr Tyr Cys Gln Gln Met
    210                 215                 220
Arg Gly Arg Pro Pro Thr Phe Gly Gln Gly Thr Lys Val Glu Ile Lys
225                 230                 235                 240
Glu Phe Ser Ser Ser Ser Gly Ser Ser Ser Gly Ser Ser Ser Ser Ser
                245                 250                 255
Gly Ser Pro Gly Gln Gly Thr Gln Ser Glu Asn Ser Cys Thr His Phe
            260                 265                 270
Pro Gly Asn Leu Pro Asn Met Leu Arg Asp Leu Arg Asp Ala Phe Ser
            275                 280                 285
Arg Val Lys Thr Phe Phe Gln Met Lys Asp Gln Leu Asp Asn Leu Leu
        290                 295                 300
Leu Lys Glu Ser Leu Leu Glu Asp Phe Lys Gly Tyr Leu Gly Cys Gln
305                 310                 315                 320
Ala Leu Ser Glu Met Ile Gln Phe Tyr Leu Glu Glu Val Met Pro Gln
                325                 330                 335
Ala Glu Asn Gln Asp Pro Asp Ile Lys Ala His Val Asn Ser Leu Gly
            340                 345                 350
Glu Asn Leu Lys Thr Leu Arg Leu Arg Leu Arg Arg Cys His Arg Phe
            355                 360                 365
Leu Pro Cys Glu Asn Lys Ser Lys Ala Val Glu Gln Val Lys Asn Ala
        370                 375                 380
Phe Asn Lys Leu Gln Glu Lys Gly Ile Tyr Lys Ala Met Ser Glu Phe
385                 390                 395                 400
Asp Ile Phe Ile Asn Tyr Ile Glu Ala Tyr Met Thr Met Lys Ile Arg
                405                 410                 415
Asn
```